United States Patent [19]
Delp et al.

[11] Patent Number: 5,682,886
[45] Date of Patent: Nov. 4, 1997

[54] COMPUTER-ASSISTED SURGICAL SYSTEM

[76] Inventors: Scott L. Delp, 2728 Woodbine; J. Peter Loan, 3233 Harrison St., both of Evanston, Ill. 60201; Craig B. Robinson, 3307 N. Kenmore Ave., Apt. Garden-Front, Chicago, Ill. 60657; Arthur Y. Wong, 826½ Washington St., #2E, Evanston, Ill. 60202; S. David Stulberg, 505 N. Lake Shore Dr., Chicago, Ill. 60611

[21] Appl. No.: 578,497

[22] Filed: Dec. 26, 1995

[51] Int. Cl.[6] .................................................. A61B 5/00
[52] U.S. Cl. .................. 128/653.1; 128/920; 128/922; 623/16; 623/18; 623/66; 382/131
[58] Field of Search .................................... 128/898, 774, 128/653.1, 654, 920, 922, 924; 606/97, 99, 53, 60, 76, 96; 382/131, 132, 153, 285, 287, 289, 108, 190, 195, 203, 204; 364/413.13, 413.19, 413.14, 413.15, 522; 623/16, 20, 18, 22, 27, 36, 39, 66; 395/924, 123, 119, 120; 378/205

[56] References Cited

U.S. PATENT DOCUMENTS

| | | |
|---|---|---|
| 4,436,684 | 3/1984 | White . |
| 4,822,365 | 4/1989 | Walker et al. . |
| 4,841,975 | 6/1989 | Woolson . |
| 4,882,679 | 11/1989 | Tuy et al. . |
| 4,936,862 | 6/1990 | Walker et al. . |
| 4,979,949 | 12/1990 | Matsen, III et al. . |
| 5,007,936 | 4/1991 | Woolson . |
| 5,086,401 | 2/1992 | Glassman et al. . |
| 5,099,846 | 3/1992 | Hardy . |
| 5,154,717 | 10/1992 | Matsen, III et al. . |
| 5,230,623 | 7/1993 | Guthrie et al. . |
| 5,236,432 | 8/1993 | Matsen, III et al. . |
| 5,299,288 | 3/1994 | Glassman et al. . |
| 5,305,203 | 4/1994 | Raab . |
| 5,383,454 | 1/1995 | Bucholz . |

OTHER PUBLICATIONS

Lea, J.T., Mills, A., Peshkin, M.A., Watkins, D., Kienzle III, T.C., & Stulberg, S.D., "Registration and Immobilization for Robot–Assisted Orthopaedic Surgery," Proceedings of the First International Symposium on Medical Robotics and Computer Assisted Surgery, MRCAS, vol. 1, Sessions I–III, pp. 63–68 (1994).

Fada, M., Wang, T., Marcacci, M., Martelli, S., Dario, P., Marcenaro, G., Nanetti, M., Paggetti, C., Visani, A., & Zaffagnini, S., "Computer–Assisted Knee Arthroplasty at Rizzoli Institutes," Proceedings of the First International Symposium on Medical Robotics and Computer Assisted Surgery, MRCAS, vol. 1, Sessions I–III, pp. 26–30 (1994).

Besl, P.J., & McKay, N.D., "A Method of Registration of 3–D Shapes," IEEE Transactions on Pattern Analysis and Machine Intelligence, vol. 14, No. 2, pp. 239–256 (Feb. 1992).

(List continued on next page.)

*Primary Examiner*—Marvin M. Lateef
*Assistant Examiner*—Eleni Mantis Mercader
*Attorney, Agent, or Firm*—Schiff Hardin & Waite

[57] ABSTRACT

A method for planning surgery on a body portion is provided in the steps of gathering image data, storing the image data, reading the image data into a computer, generating a three-dimensional computer model of the body portion from the image data, identifying anatomical features relevant to the surgery, and defining at least one desired correction to anatomical structures to be accomplished by the surgery. Also, a method for performing surgery on a body portion is provided in the steps of loading surgical plan data into a computer, registering a three-dimensional computer model of the body portion stored in the surgical plan data to the body portion, providing at least one surgical tool, positioning the surgical tool relative to the body portion and performing the surgery. Further, a jig assembly is provided in the form of a femoral docking jig, a femoral contouring jig, and a tibial jig.

55 Claims, 19 Drawing Sheets

OTHER PUBLICATIONS

Kass, M., Witkin, A., & Terzopoulos, D., "Active Contour Models," International Journal of Computer Vision, pp. 321–331 (1988).

Canny, J., "A Computational Approach to Edge Detection," IEEE Transactions on Pattern Analysis and Machine Intelligence, vol. PAMI 8, No. 6, pp. 679–698 (Sep. 1986).

ISG Technologies Inc., 6509 Airport Road, Toronto, Ontario Canada, 14V 157 14161, "Technical Specifications: The Viewing Wand™."

Integrated Surgical Systems, Inc., 829 West Stadium Lane, Sacramento, California, 95834, "Robodoc™ Surgical Assistant System."

Picker International, Inc., World Headquarters, 595 Miner Road, Cleveland, Ohio, 44143, "ViewPoint™ Workstation for Image–Guided Surgery: Product Data."

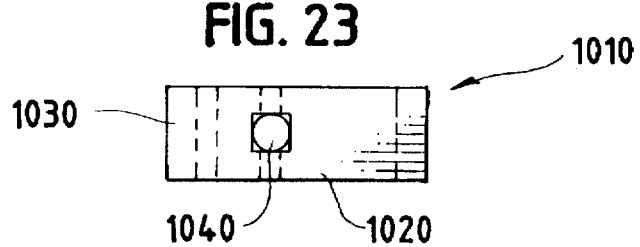
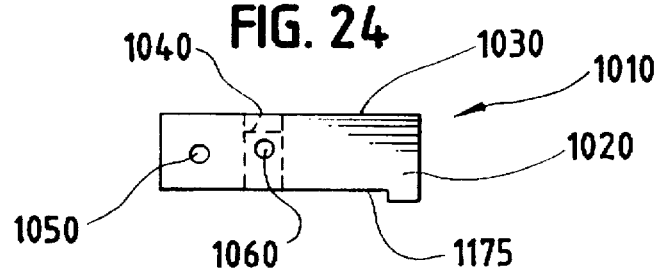
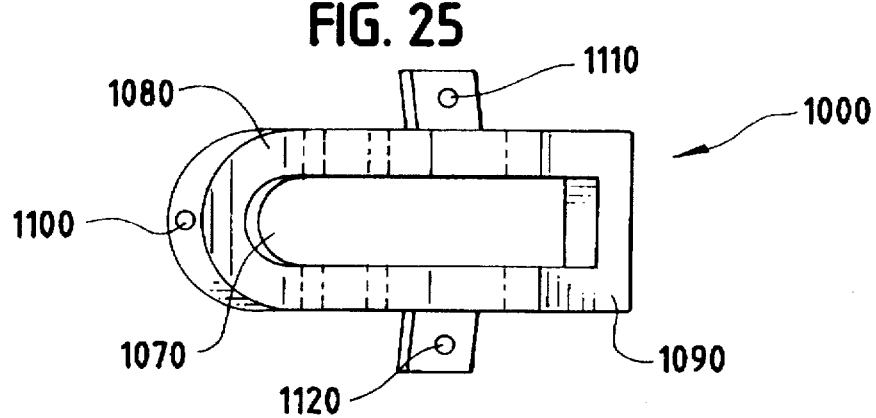
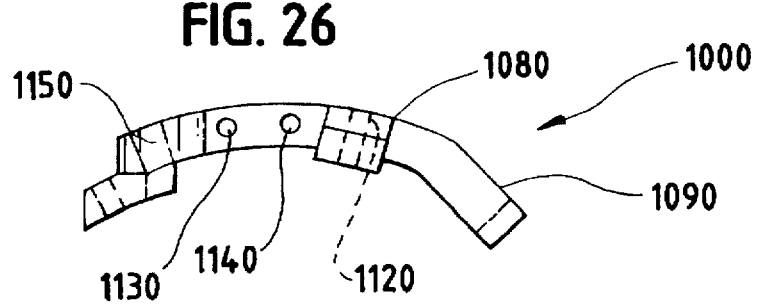

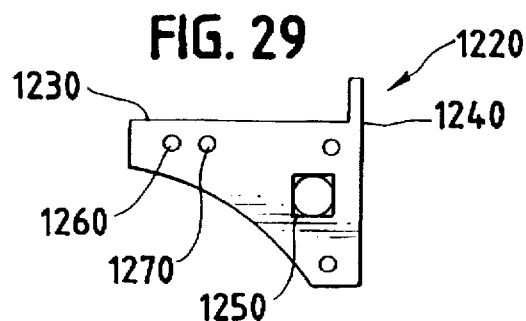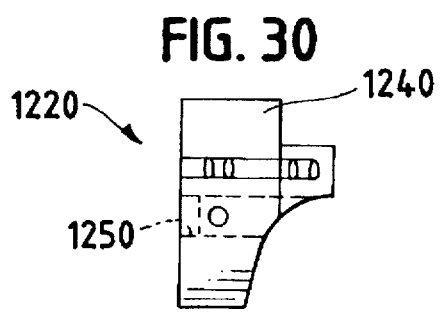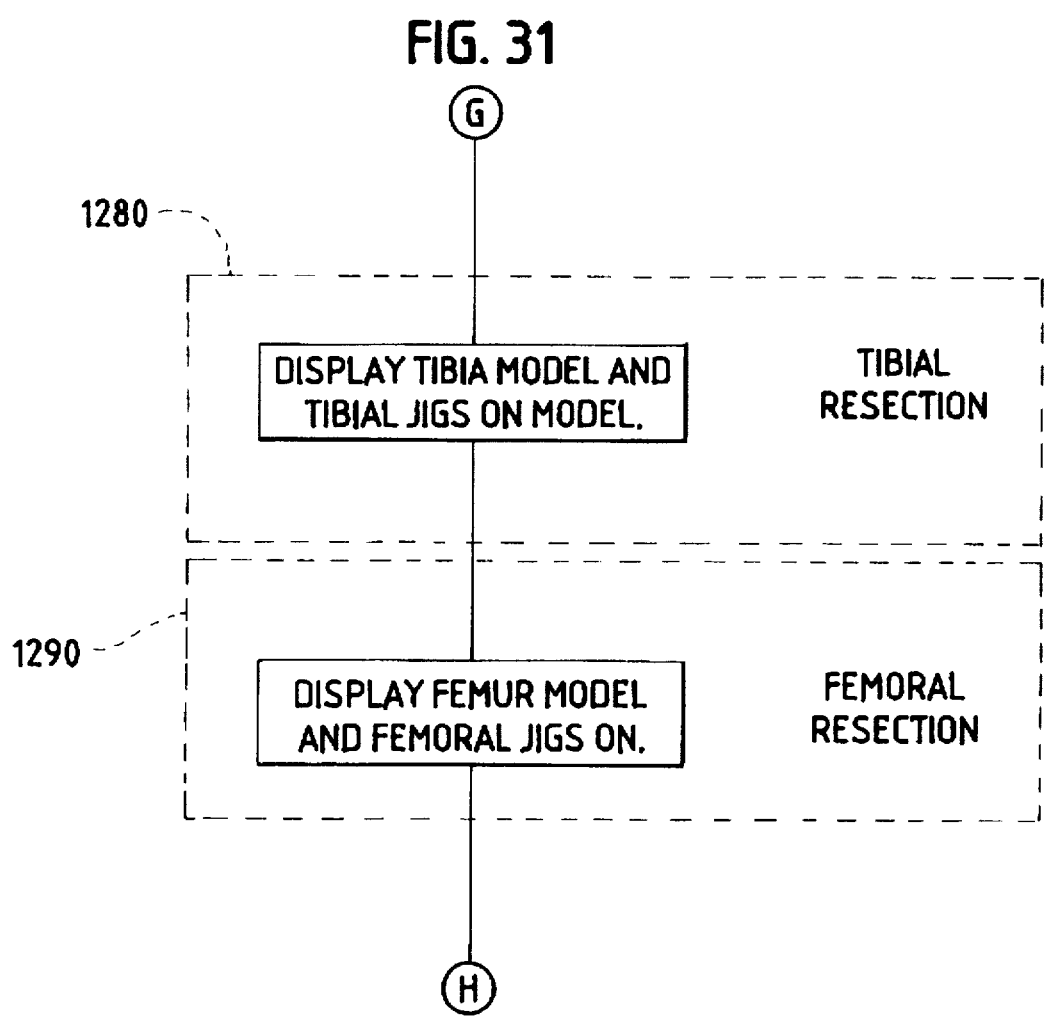

COMPUTER-ASSISTED SURGICAL SYSTEM

BACKGROUND OF THE INVENTION

This invention relates generally to computer-assisted surgical systems, and in particular to a computer-assisted knee replacement system used to achieve accurate limb alignment with minimal surgical invasiveness.

One application for computer-assisted surgical systems is in the field of knee arthroplasty. Knee arthroplasty is a surgical procedure in which the articular surfaces of the femur and tibia (and the patella, in the case of tricompartmental knee arthroplasty) are cut away and replaced by metal and/or plastic prosthetic components. The goals of knee arthroplasty are to resurface the bones in the knee joint and to reposition the joint center on the mechanical axis of the leg. Knee arthroplasty is performed to relieve pain and stiffness in patients suffering from joint damage caused by osteo-, rheumatoid, or post-traumatic arthritis. In 1993, approximately 189,000 knee arthroplasties were performed in the United States, and this number is expected to increase over the next decade as the U.S. population ages.

More than 95% of knee arthroplasties performed in the U.S. are tricompartmental. Tricompartmental knee arthroplasty ("TKA") involves the replacement of all the articular surfaces of the knee joint, and is performed when arthritis is present in two or more of the three compartments of the knee: medial (toward the body's central axis), lateral (away from the body's central axis), and patello-femoral (frontal).

The remaining knee arthroplasties are unicompartmental knee arthroplasties ("UKA"). UKAs involve the replacement of the articular surfaces of only one knee compartment, usually the medial. UKAs are indicated when arthritis is present in only one compartment and when the patellar surface appears healthy.

UKAs have several advantages over TKAs. These include the preservation of more patient anatomy, increased knee stability, less complicated revision surgery, and the potential for installation through a smaller incision, as compared with a TKA. A TKA requires the resection of the entire tibial plateau, both condyles of the femur, and the posterior side of the patella, because all compartments of the knee are replaced. As a result, in TKAs, the anterior cruciate ligament, which is attached to the front of the tibial plateau, usually is removed, severely reducing the stability of the knee after the operation. In contrast, during UKAs, only one compartment is replaced, and thus only one side of the tibial plateau is removed. As a result, the anterior cruciate ligament may be preserved, allowing for increased knee stability. In addition, if a revision surgery is required, more natural bone stock is present on which to place the revision components. Finally, since the resections and components used in UKAs are smaller, minimally-invasive surgical procedures may be applied.

In the late 1970s, there were reports of high failure rates for UKAs due to problems such as improper alignment. One study, for example, reported that 10% of UKA patients needed revision surgery because one or both of the other knee compartments degenerated due to the presence of polyethylene particles that flaked off the prosthetic components. Overcorrection of the varus/valgus deformity, which is the angle between the mechanical axis of the femur and the mechanical axis of the tibia in the anterior/posterior ("A/P") plane, was one suspected cause of the excessive component wear.

In contrast, many recent studies have indicated high success rates for UKAs. These studies report that the incidence of failure for UKAs is comparable to or less than that for TKAs. The higher success rates for UKAs are likely due to the use of thicker tibial components than used in earlier UKAs, the use of component materials that are less susceptible to wear than earlier materials, and better alignment of the components by the surgeon so as to not overcorrect varus/valgus deformity.

Despite those recent studies, in many cases where UKAs are indicated, orthopaedic surgeons in the U.S. still perform TKAs. This conservative attitude towards UKAs is believed to be the result of several factors, such as the use of poor instrumentation to install the implants, concern over arthritis spreading to other compartments, and the early mixed reviews of UKA outcomes in the literature. Because of this conservative attitude, the benefits of UKAs are not realized by many patients.

Although UKA success rates are higher than they were 20 years ago, there are still important problems in UKA and TKA performance. For example, alignment of the femoral and tibial prosthetic components with respect to the bones and to each other currently involves the use of purely mechanical instrumentation systems. Typical femoral instrumentation consists of an intramedullary rod (a metal rod that is aligned with the femoral shaft via insertion into the medullary canal of the femur) and several slotted cutting jigs for guiding a saw blade used to resect the bone. The surgeon aligns the jigs first by drilling a hole through the center of the distal end of the femur into the medullary canal, which runs the length of the femoral shaft, and then inserts the intramedullary rod into the canal. Thereafter, the surgeon removes the rod from the femur, and slides a cutting guide onto the rod. The surgeon next reintroduces the rod into the medullary canal, and positions the cutting guide against the distal end of the femur. To account for the fact that the rod is oriented along the femoral shaft, which does not correspond to the mechanical axis of the femur, the cutting guide is usually offset by a predetermined and fixed distance from the rod in the A/P pirate. The offset is provided to allow a distal cut to be made that is perpendicular to the mechanical axis of the femur, thus correcting any varus/valgus deformity. The depth of the distal cut is usually adjustable in discrete intervals: some systems have cutting blocks with slots at multiple depths, while others have cutting blocks with pin holes at multiple depths allowing the entire block to be moved up or down on a set of parallel pins. The remaining cuts vary depending on the geometry of the implant being installed. The depth and orientation of all these cuts, however, are determined by the cuts already made and/or by visual means.

Tibial instrumentation consists of an extramedullary rod (a metal rod that the surgeon aligns with the tibial shaft via external anatomical landmarks) and a slotted cutting guide. The mechanical axis of the tibia is assumed to run along the tibial shaft. The surgeon places the cutting jig at the top of the rod, with the cutting surface perpendicular to the rod. The depth of the cut is adjusted by moving the jig along the rod. The surgeon clamps the bottom of the rod around the ankle, just proximal to the malleoli (which form the distal portion of the tibia and fibula).

The instrumentation systems just described suffer from certain problems. Femoral varus/valgus alignment, for example, is determined by a discrete and predefined offset from the femoral shaft, which may not result in the desired angular correction. The amount of bone resected is adjustable, but only through slots positioned at discrete intervals of about two millimeters. Other parameters, such as rotation around the axis of the limb, must be determined visually. The tibial jig is aligned almost entirely by the surgeon's visual judgment.

Discretely adjustable alignment systems can introduce inaccuracies when an optimal resection falls between or outside of the range of predefined alternatives. The surgeon in such circumstances must decide which of the available alternatives is closest to the optimal resection. Moreover, the accuracy of visual alignment is primarily the product of the surgeon's experience in performing TKAs and UKAs. The accuracy needed in alignment of the prosthetic components with respect to the bones is still being debated, but it has been shown that misalignment of the components can cause excessive component wear. As a result, revision surgery often is necessary.

Moreover, because current UKA instrumentation systems are, for the most part, modified TKA instrumentation systems, some of the possible benefits unique to UKAs have not been realized. For example, because UKA components are less than half the size of TKA components, they can be implanted using a smaller surgical incision. However, many of the instrumentation sets for UKAs still require full exposure of the knee, and the use of an intramedullary rod, which can be a source of complications. Thus, the benefits of limited exposure, such as shorter operating room ("OR") time, decreased healing time, and less morbidity, have not been realized with current UKA techniques.

New technologies, in addition, reveal that existing procedures may be improved. Recent advances in medical imaging technology, such as computed tomography ("CT") and magnetic resonance ("MR") imaging, have made it possible to display and manipulate realistic computer-generated images of anatomical structures. These advances have had immediate practical applications to surgery simulation, i.e., computer-modeled surgical procedures used to plan, teach, or aid surgery. Many of the early simulations are related to planning and evaluating neurosurgery. More recently, three-dimensional reconstructions from CT data have been used to plan total hip reconstructions, osteotomies (a removal of a piece of bone to correct a deformity), and allograft procedures (tissue graft), and to design custom prostheses. Such surgical planning systems can be used to develop three-dimensional models, which help surgeons properly size and "pose" surgical tools and prosthetic components in the body. (As used herein, "pose" refers to the position and the orientation of a structure, and may be used as a noun or as a verb.) Most systems, however, have no way of transferring this information into the operating room. The computer assists in the planning, but not in the implementation, of the procedure. For the computer to assist in the implementation of the surgical plan, the models used in the surgical planning procedure must be "registered" to the patient intraoperatively. Registration is the process of defining a geometric transform between the physical world and a computer model. In this way, the computer can direct the placement of the tools and prosthetic components relative to the patient.

Some computer-assisted surgery systems combine surgical planning software with a registration method to implement surgical plans. These systems have been applied to the planning and implementation of orthopaedic procedures. For example, the "Robodoc" hip replacement system from Integrated Surgical Systems (Sacramento, Calif.) uses a computer-based surgical plan with a robotic manipulator to perform intraoperative registration and some of the bone resections needed for hip replacement. The Robodoc system has been tested in the operating room and has produced accurate bone resections, but the system has several important limitations. It is expensive, for example, and must be operated by a specially-trained technician. It also adds substantially to OR time, increasing the cost of using the system. Another problem is that the Robodoc system uses a pin-based registration method. The pins, called "fiducials," are inserted into the patient's bones prior to imaging. Registration is achieved by aligning the fiducials in the image data with the fiducials on the patient. Pin-based registration requires an additional surgical procedure to insert the pins, causing additional pain to the patient, and lengthening the patient's rehabilitation time.

The present invention is intended to overcome the disadvantages associated with current knee arthroplasty procedures, surgical planning systems, and computer-assisted surgery systems. The present invention determines optimal alignment of resections preoperatively, and uses computer modeling techniques to help the surgeon achieve that alignment. Moreover, smaller jigs are used in the present invention, and therefore, smaller incisions are made in the patient's leg. The present invention also plans the surgical procedure preoperatively, and assists in implementing the plan. Further, the present invention is less expensive than many prior art systems, and makes it possible to use pinless registration methods. Thus, the present invention represents a significant solution to many problems experienced in the field.

SUMMARY OF THE INVENTION

The invention is embodied in a method for planning surgery on a portion of a body with the goals of improving the accuracy of the surgery and reducing the risks associated with surgery. This method comprises the steps of gathering image data of the portion of a body using a radiant energy means for gathering image data. The image data is stored in a memory means. The stored image data then is read into a computer having a visual display for displaying images generated in at least one process step. The system uses the image data to generate a three-dimensional computer model of the body portion using a modeling means, and identifies anatomical features relevant to the surgery on the three-dimensional computer model. Finally, the system defines at least one desired correction to the anatomical structures to be accomplished by the surgery. In one embodiment of the invention, the method for planning surgery is used to plan unicompartmental knee arthroplasty surgery.

The invention further is embodied in a method of performing surgery on a portion of a body with the goals of improving the accuracy of the surgery and reducing the risks associated with surgery. The method comprises the steps of loading surgical plan data stored in a memory means into a computer having a visual display for displaying images generated in at least one process step. The surgical plan data comprises a three-dimensional computer model of a body portion, and data relating to at least one prosthesis of defined size and position relative to the body portion. The system then registers the three-dimensional computer model of the body portion to the actual body portion using a registration means. The system next provides at least one surgical tool that has a defined relationship relative to the prosthesis defined in the surgical plan data, the relationship defining a desired pose for the surgical tool relative to the body portion. Finally, the system allows the user to pose the surgical tool relative to the body portion in the desired pose, and the surgery is performed. In one embodiment of the invention, the method for performing surgery is used to perform unicompartmental knee arthroplasty. In another embodiment of the invention, the method for performing surgery further comprises the step of performing at least one resection on the body portion, wherein the resection is performed using a burring device.

The invention also is found in a jig assembly for guiding a device used to resect a femur and a tibia. The jig assembly comprises a femoral docking jig having a body, and a first aperture for receiving a positioning device. The jig assembly also comprises a femoral contouring jig that has a second aperture for receiving the femoral docking jig and at least one surface for guiding a device used to resect the femur and the tibia. Finally, the jig assembly comprises a tibial jig having a horizontal cutting guide surface and a vertical cutting guide surface to guide the device used to resect the femur and the tibia, and a docking hole for receiving a positioning device. In another embodiment where the tibial prosthesis employs a fixation post, a tibial post hole jig also is positioned.

It is an object of the invention to provide a computer-assisted surgical system that costs substantially less than current systems.

It is another object of the invention to provide a computer-assisted surgical system that requires shorter OR time than current systems.

Another object of the invention is to provide a computer-assisted surgical system method that decreases patient complications.

It is another object of this invention to provide a computer-assisted surgical system that decreases the length of a patient's hospital stay.

Another object of the invention is to provide a computer-assisted surgical system that decreases a patient's rehabilitation time.

Another object of the invention to provide a computer-assisted surgical system that allows surgeons to install unicompartmental knee implants more accurately and less invasively than is possible with current systems, thereby increasing implant longevity and improving knee function.

Still another object of the invention is to provide a method of performing knee arthroplasty that allows for more accurate alignment of the prosthetic components with respect to the bones than is currently available using mechanical instruments with slots distanced at discrete intervals.

Another object of the invention is to provide a method of performing knee arthroplasty that does not require the use of an intramedullary rod in the femur.

Another object of the invention is to provide a method for implanting unicompartmental knee arthroplasty components using a smaller surgical incision than is used by current methods.

Another object of the invention is to provide a method of registering a computer model and surgical plan to a patient's body using a coordinate measuring machine.

Another object of the invention is to provide a method of registering a computer model and surgical plan to a patient without the need for an additional surgical procedure.

Still another object of the invention is to provide cutting jigs that are smaller than current cutting jigs, thereby requiring smaller incisions for placement.

Another object of the invention is to provide cutting jigs each of which can guide multiple bone resections necessary for UKAs, thereby reducing the number of cutting jigs required to perform UKAs.

BRIEF DESCRIPTION OF THE DRAWINGS

FIG. 23 is a top view of a femoral docking jig.

FIG. 24 is a side view of a femoral docking jig.

FIG. 25 is a top view of a femoral contouring jig.

FIG. 26 is a side view of a femoral contouring jig.

FIG. 29 is a top view of a tibial cutting jig.

FIG. 30 is a rear view of a tibial cutting jig.

FIG. 31 is a flow chart illustrating one sequence of steps that is useful in the invention to resect a tibia and to resect a femur.

DETAILED DESCRIPTION OF THE INVENTION

While the invention will be described in connection with a system for performing UKAs, this description is not intended to limit the invention to that application. Rather, it is intended to cover other surgeries and applications to which the technology may be beneficially applied. For example, the invention can be used in connection with TKAs, revision knee surgery, and other surgeries. Likewise, the invention can be used for other joint replacements that involve placing a rigid prosthetic component, or surgical instrumentation, on a bone. The invention also may be used in surgeries to install screws into broken hips or to correct other bone injuries. Persons skilled in the art will be able to adapt the invention to other applications with ready facility. Moreover, the invention need not be limited to the exact order of the steps specified herein, except to the extent that a step requires information that is obtained in a previous step. For example, in the case of UKA surgery described herein, steps that are to be performed on the tibia may occur before steps to be performed on the femur, notwithstanding the ordering of steps that follows below.

Figure 1:
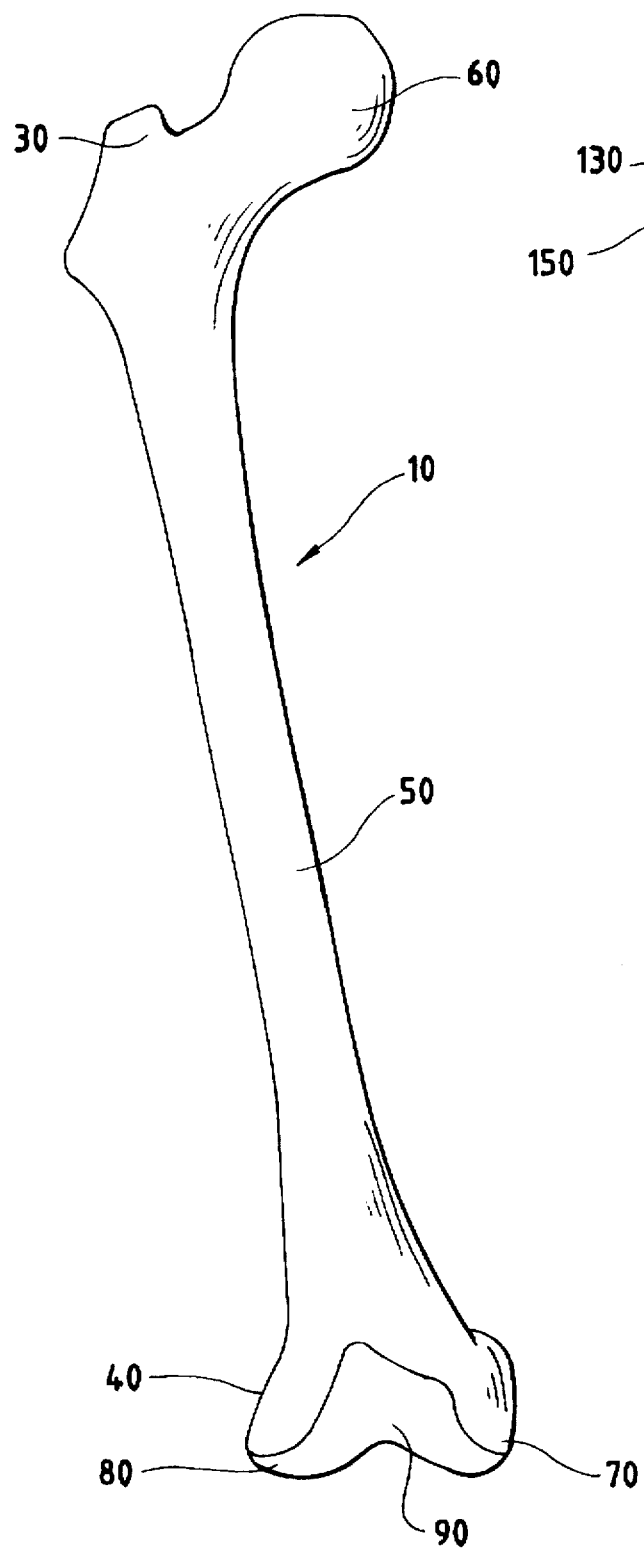
FIG. 1 is a front plan view of a femur.
Figure 2:
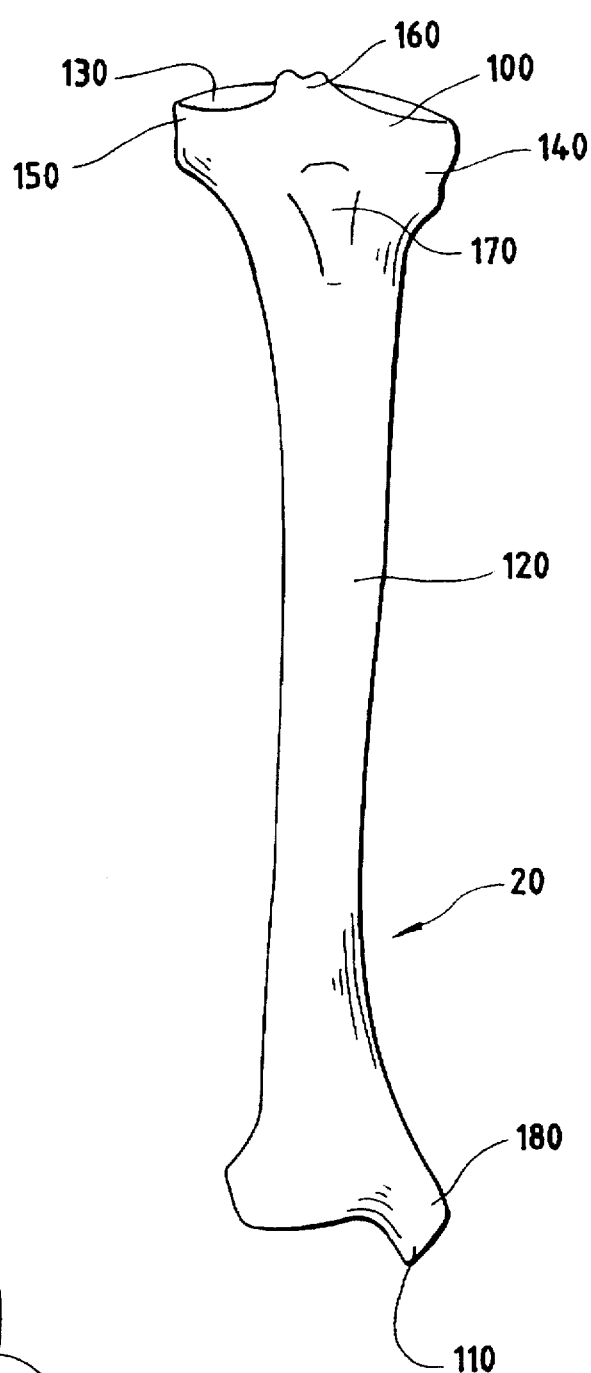
FIG. 2 is a front plan view of a tibia.

UKA surgery involves two bones shown in FIGS. 1 and 2: the femur 10 and the tibia 20. As shown in FIG. 1, the femur 10 extends from the hip (not shown) to the tibia 20, and has a top 30 and bottom 40 separated by a long shaft 50. The top 30 of the femur 10 is dominated by a femoral head 60, which is nearly spherical, and which extends at an angle of about 135 degrees from the shaft 50 of the femur 10 towards the center of the body, to fit within a hip socket. The bottom 40 of the femur 10 consists of a medial condyle 70 and a lateral condyle 80, which are rounded knobs separated by a smooth depression in front, called the trochlea 90, and a large notch in the rear (not shown), called the intercondylar notch. The medial condyle 70 is the condyle that is closest to the center axis of the body, and the lateral condyle 80 is the furthest from the center axis of the body.

Figure 3:
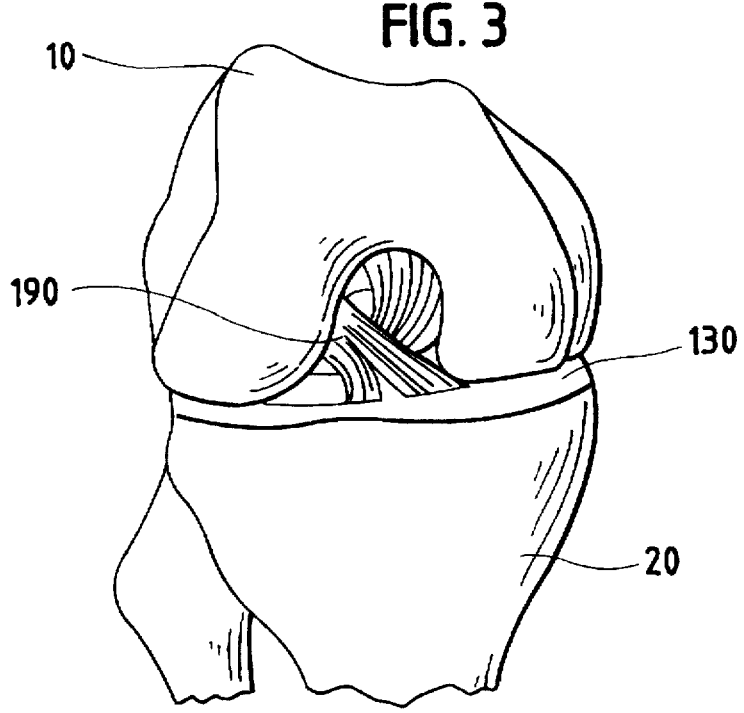
FIG. 3 is a front elevational view of the knee joint, showing the bottom of a femur, with the patella deleted to expose the femur, tibia, and ligaments.

Turning now to FIGS. 2 and 3, the tibia 20 extends from the femur 10 to the ankle (not shown), and has a top 100 and bottom 110 separated by a long shaft 120. The top 100 of the tibia 20, known as the tibial plateau 130, consists of a medial condyle 140 and lateral condyle 150, which are concave, and separated by a small ridge, called the tibial spine 160. The tibial medial condyle 140 and lateral condyle 150 articulate with the corresponding femoral medial condyle 70 and lateral condyle 80 of the femur 10. Several centimeters below the tibial plateau 130 is the tibial tuberosity 170, which is a mass that protrudes slightly from the tibia's anterior surface down from the top portion 100 of the tibia 20. The bottom 110 of the tibia 20 consists of a medial malleolus 180, which is a bony protuberance that protects the joint between the tibia 20 and the talus (not shown), a small bone just below the tibia 20. The anterior cruciate ligament 190 connects the lateral condyle 80 of the femur 10 and the anterior part of the tibial plateau 130, and provides stability to the knee.

Figure 4:
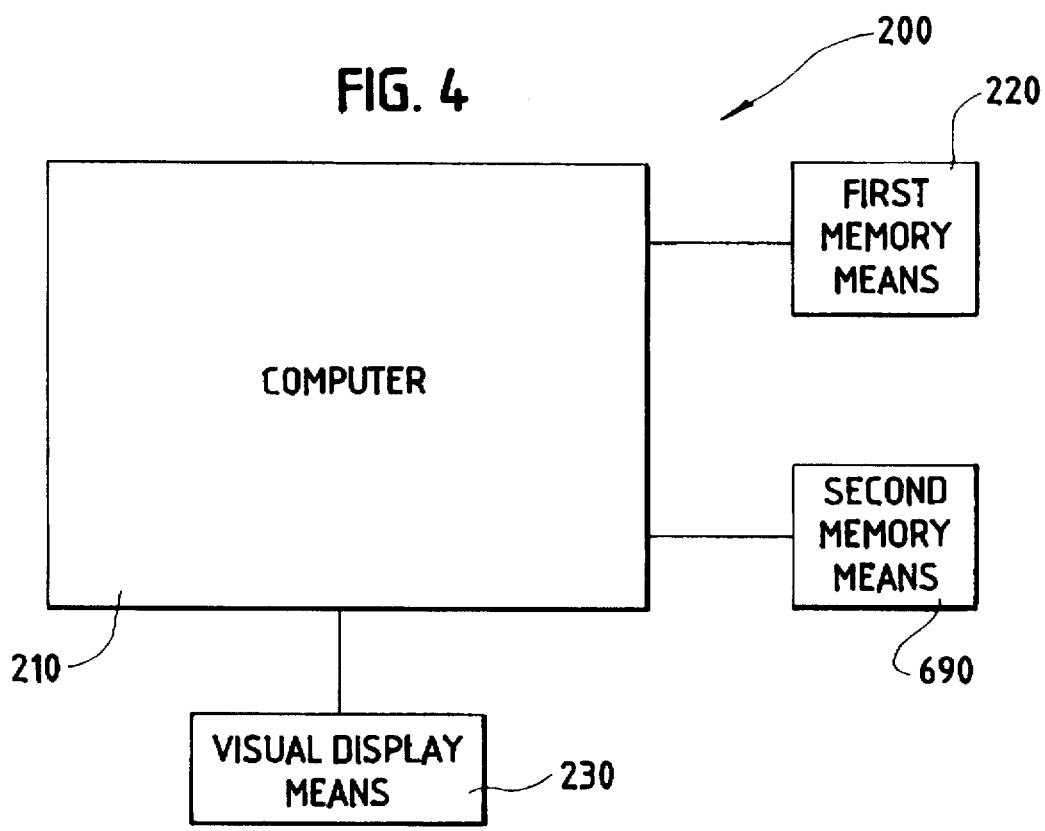
FIG. 4 is a functional block diagram of the planning computer and associated hardware used in the invention.

The system of the present invention can be described as two subsystems: (1) a planning subsystem and (2) a procedure subsystem. The planning subsystem hardware, as shown in FIG. 4, first is composed of a planning workstation 200, which is a computer 210 interfaced with a memory means 220 for storing image data so that the image data may be read into the computer 210. The memory means 220 is of any suitable form, such as electronic storage media, electronically erasable storage media, electromagnetic storage media, magnetic storage media, optical storage media, or magnetic-optical storage media. The computer 210 also includes a visual display means 230 for visually displaying images generated in at least one process step, but preferably displays images generated in more than one process steps. The visual display means 230 is preferably a raster display means; however, other visual display means 230 (such as a vector display means) may be used without departing from the instant invention. An embodiment of the instant invention uses a Silicon Graphics Indigo 2 workstation as the computer 210; however, other computers having adequate graphics and processing capability may be used without departing from the invention. The planning subsystem also is composed of preoperative planning software used to process medical image data, build a three-dimensional computer model of the patient's leg from that data, align the model of the limb, and size and place the representations of prosthetic components.

Figure 5:
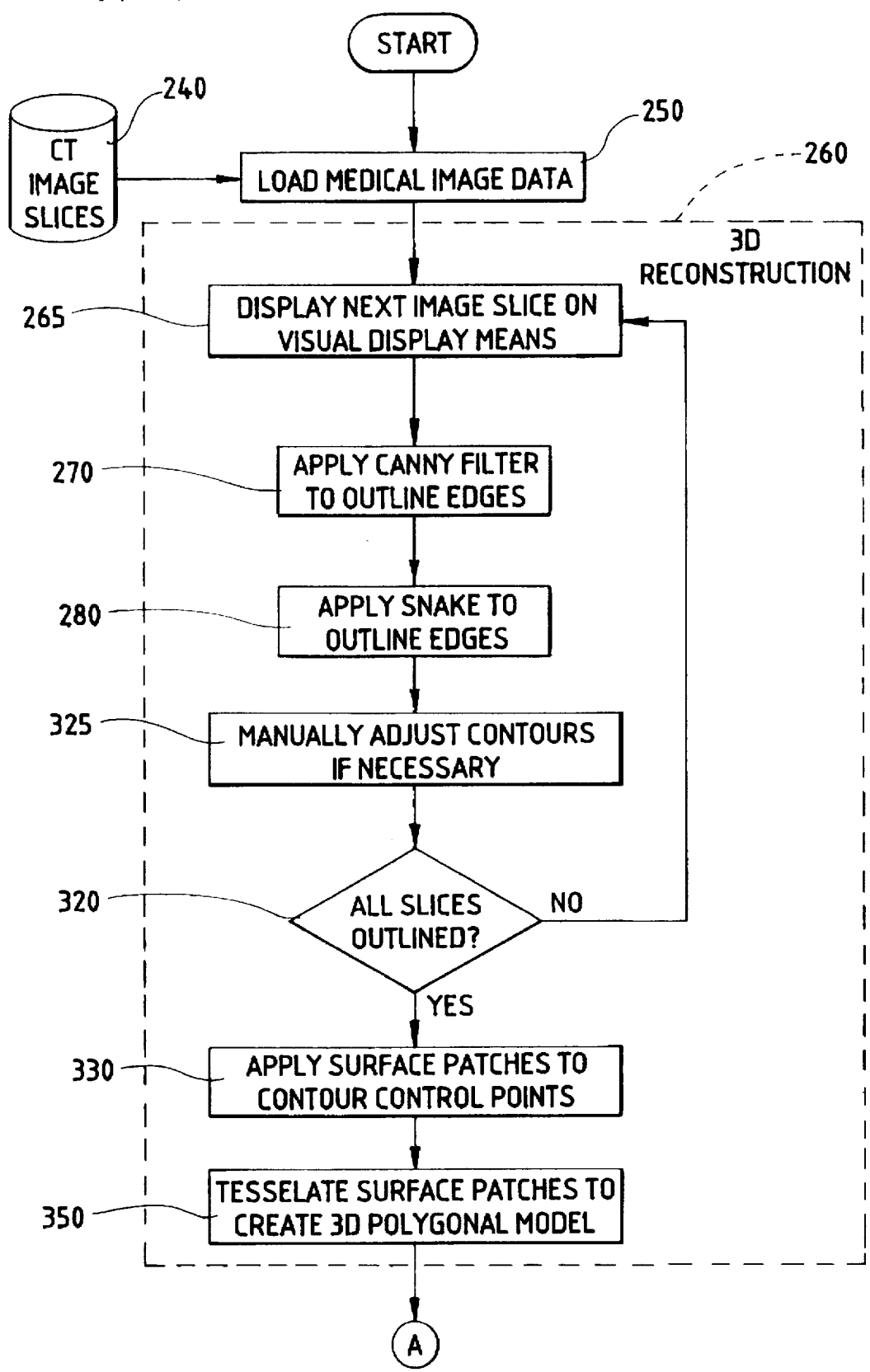
FIG. 5 is a flow chart illustrating one sequence of steps that is useful in the invention to generate a three-dimensional computer model of a patient's anatomy.

Turning now to FIG. 5, in the first step of the planning subsystem, the operator gathers image data of the patient's leg using a radiant energy means for gathering image data, as reflected by block 240. The radiant energy means is preferably a CT device well-known in the art; however, other radiant energy means, such as MR imaging devices and X-ray devices, may be used without departing from the instant invention. When using the preferred CT device, a conventional scanning protocol is employed to collect image data. Thus, in one embodiment, the protocol collects the following image data with the knee in full extension to create a three-dimensional computer model of the patient's bones: ten 1.5 mm CT image "slices" (or, in other words, ten slices 1.5 mm apart) at the hip, several 50 mm slices through the shaft 50 of the femur 10, seventy 1.5 mm slices at the knee, several 50 mm slices through the shaft 120 of the tibia 20, and ten 1.5 mm slices at the ankle. A "slice" is a two-dimensional image of a body portion taken in the transverse plane (as seen looking down from above the head) by an imaging means, preferably an X-ray. The number of slices that are taken for the femur 10 and tibia 20 will depend on the length of those bones, but enough slices must be taken to create an accurate three-dimensional computer model of those bones. For a normal-sized leg, the operator will take approximately fifty slices for each of the femur 10 and tibia 20. As already noted, image data collection using other imaging techniques, for the purpose of developing three-dimensional computer models of the imaged body, is well-known in the field. The collected image data then is stored on the memory means 220.

After the image data is collected, the system uses the data to generate a three-dimensional computer model of the bones. First, an operator interfaces the memory means 220 to the computer 210, and locates the image data in the memory means 220. The planning software then, as reflected by block 250, reads the image data into the planning computer 210. After the image data has been loaded, the operator may view the image data to confirm its quality and accuracy. The operator then, as reflected by block 260, directs the use of a modeling means for creating three-dimensional anatomical models from image data. The image data represent discrete areas corresponding to the relevant anatomical structures (for UKAs, those anatomical structures are the femur 10 and tibia 20), wherein boundaries defining each anatomical structure are determined by variations in the image data, such as color or brightness gradients (variations in color or light-to-dark changes) The operator uses the modeling means to locate the boundaries that define the surfaces of the anatomical structure, and to define continuous curves (or, in other words, outlines) corresponding to those boundaries, to create the three-dimensional computer model of the anatomy from those continuous curves. The operator also may locate anatomical landmarks in the image data for use in surgical planning.

(As used in this application, the term "three-dimensional model," whether applied to a bone model or to images corresponding to other structures, means a set of relevant coordinates in three-dimensional space. Thus, a three-dimensional model of a body portion may be a surface reconstruction of the relevant anatomical structures (such as bones), or relevant portions of those structures where less than the entire structure is relevant to the surgical procedure, or a selection of critical and/or noncritical points in space that may be used to define the surgical procedure. A three-dimensional model of a prosthesis may be a surface reconstruction of the actual prothesis, or a selection of critical points on the prosthesis useful to determine required dimensions and geometry.)

In the preferred embodiment, the modeling means first uses two algorithms to define a set of edges in the image data, and to create active contours that fit those edges. The first algorithm is the Canny edge filter, which is well known in the art, and which is described in Canny, J., "A Computational Approach to Edge Detection," IEEE Transactions on Pattern Analysis and Machine Intelligence, PAMI 8(6), pp. 679–698 (1986). First, as reflected by block 265, a slice is displayed on the visual display means 230. As reflected by block 270, the Canny edge filter then defines edges in the image data by comparing variations in the image data with a reference value that is preselected to correspond to the edge of an anatomical structure. Preferably, the variations in the image data are variations in brightness; however, other variations from which the Canny edge filter can define a set of edges may be used without departing from the instant invention. In a particularly preferred embodiment, the operator can adjust the reference value to adjust for imaging variations.

Figure 6:
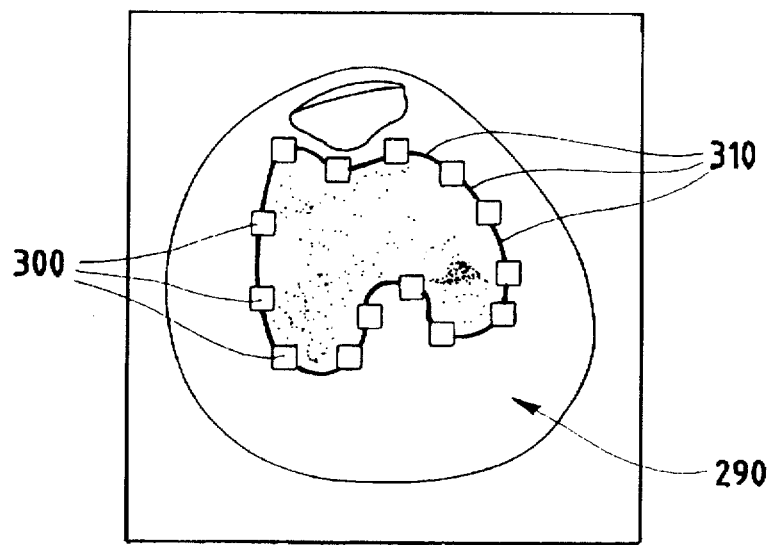
FIG. 6 is a top plan view of a CT image slice outlined by an active contour.

Turning now to FIGS. 5 and 6, the second algorithm is the "snake" algorithm, which also is well known in the art, and is described in Kass, M., Witkin, A., & Terzopoulos, D., "Active Contour Models," International Journal of Computer Vision, pp. 321–331 (1988). As reflected by block 280, the "snake" algorithm first forms a continuous boundary, called an active contour 290, which consists of a series of points 300 connected by straight lines 310. For the first slice of image data, the operator specifies the positions of these points on the image data using a pointer, such as a mouse. For each subsequent slice, the algorithm uses the points from the previous slice to define the initial position of the active contours 290. The algorithm then adjusts the sizes and shapes of the active contours 290 to fit the set of edges defined above. The active contours 290 are analogous to a closed loop of springs connected at these points 300. If a spring is near an edge in the image data, the snake algorithum moves the spring close to the edge, which also causes associated springs to move. This process continues until a best fit of the active contours 290 to the edges in the image data is obtained, as reflected by block 320.

Preferably, the snake algorithm uses two parameters to limit the movement of the active contours 290. The first parameter is a bending factor that limits how much the active contours 290 can curve in a small region. The lower the bending factor, the more the active contours 290 can curve in a small region. A high bending factor is used with poor quality image that has extraneous brightness variations so that the snake algorithm does not fit the active contours 290 to extraneous edges. The second parameter is a stretch factor, which is the resistance of the active contours 290 to having their sizes changed while their shapes remain constant. Stretching is used for changes from one slice in the image data to the next immediate slice, for which the shape in the image data will not change greatly from slice to slice, but its size will.

In the preferred embodiment, the planning software has defaults built in for the bending factor and the stretch factor. In a more preferred embodiment, the operator can adjust the defaults. Preferably, as reflected by block 325, the active contours 290 defined by the algorithm also may be adjusted by the operator to better fit and outline the edges of the anatomical structures.

Figure 7:
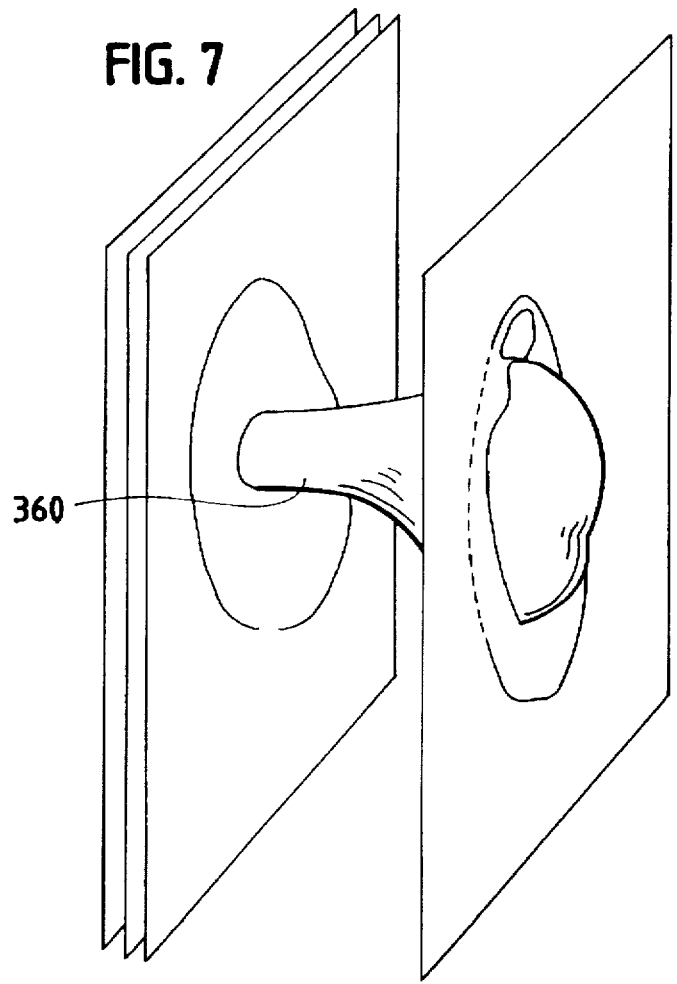
FIG. 7 is a side view of a three-dimensional computer model, based in part on the active contour shown in FIG. 6, of the top of a femur lying horizontally.

Turning now to FIGS. 5 and 7, once a particular bone has been outlined, the modeling means, as reflected by block 330, uses the points 300 of the active contours 290 to create surface patches, which are three-dimensional surfaces defined by a third-order polynomial equation that uses the three-dimensional coordinates of the points 300 as input. In one embodiment, the surface patches are Bezier patches, which are well known in the art. The modeling means, as reflected by block 350, tessellates the surface patches (i.e., resurfaces them with polygons) to form polygonal meshes 360. (The intersections of the line segments that form the polygonal meshes 360 are vertices, one of which is used to define the varus/valgus correction.) These polygonal meshes 360 represent the surface of the bone, and together form a type of three-dimensional computer model of the anatomy. Although this method for creating a three-dimensional computer model is preferred, other methods may be used without departing from the present invention. The modeling means preferably is implemented in software. The modeling means also may be used to identify the relevant anatomical structures. In one such embodiment, the user highlights relevant anatomical structures directly on the image data using a pointer, such as a mouse. The three-dimensional computer model of the body preferably is displayed on the visual display means 230.

As an alternative to the modeling means just described, the invention may use commercially-available three-dimensional reconstruction software useful to create three-dimensional models from the image data. Such software includes Allegro (ISG, Toronto, Canada); Preview (Medical Media Systems, West Lebanon, N.H.); Omniview (3D Biomedical Imaging, Inc., Fairway, Kans.); Analyze (Mayo Clinic, Rochester, Minn.); Orthodoc (Integrated Surgical Systems, Sacramento, Calif.); and 3D Render View (Picker International, Cleveland, Ohio).

It also should be understood that the invention may employ, in place of the three-dimensional models of entire bones that have been described herein, models of the articular surfaces of the knee. Still other modeling techniques use only the three-dimensional coordinates of points defining the key structures (such as the joint centers, and the boundary points defining the proper size and pose of the prosthesis) in place of three-dimensional bone models. The use of such techniques in place of the computer bone models described in detail herein is well-known to skilled persons.

Figure 8:
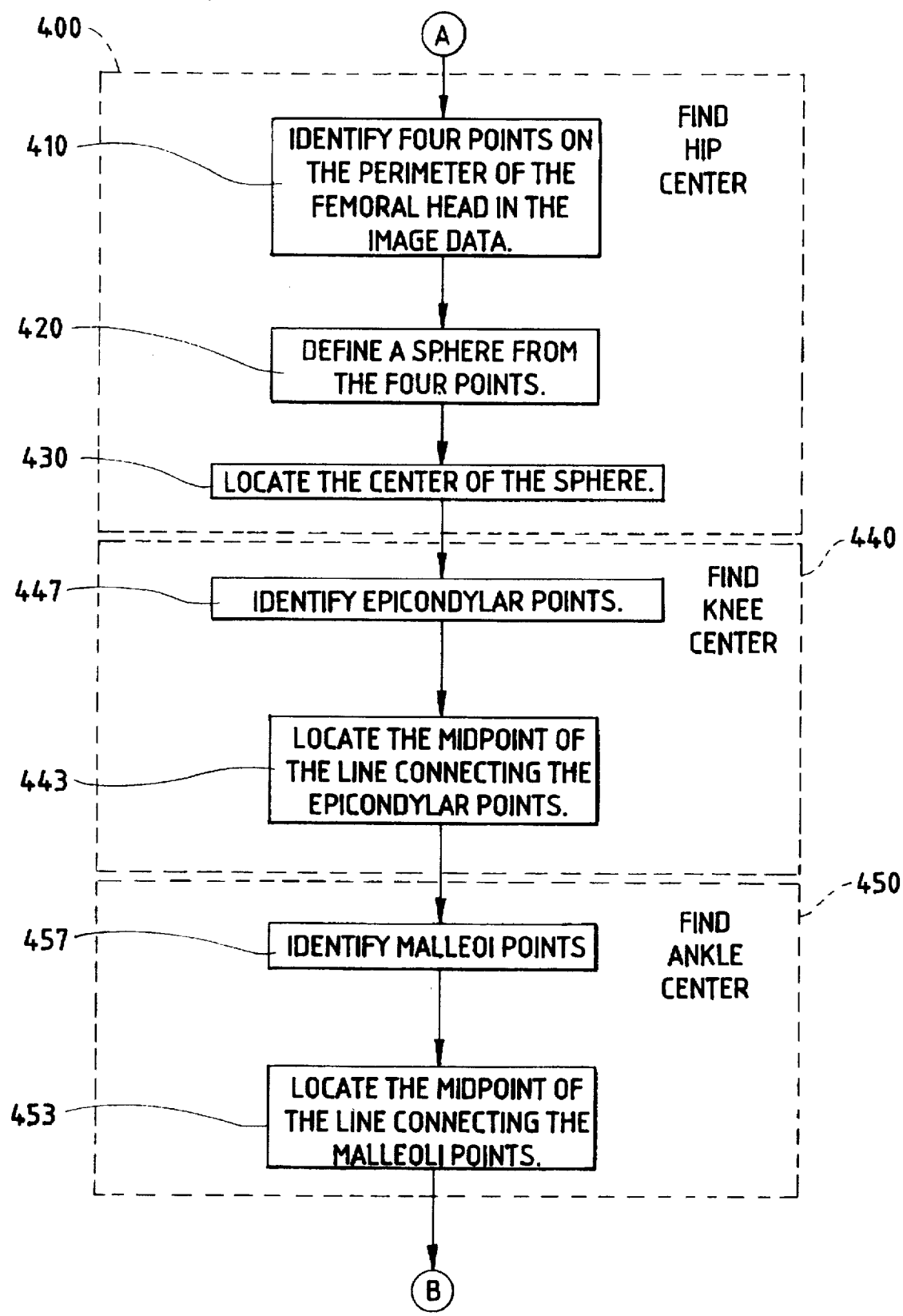
FIG. 8 is a flow chart illustrating one sequence of steps that is useful in the invention to find a hip center, a knee center, and an ankle center.
Figure 9:
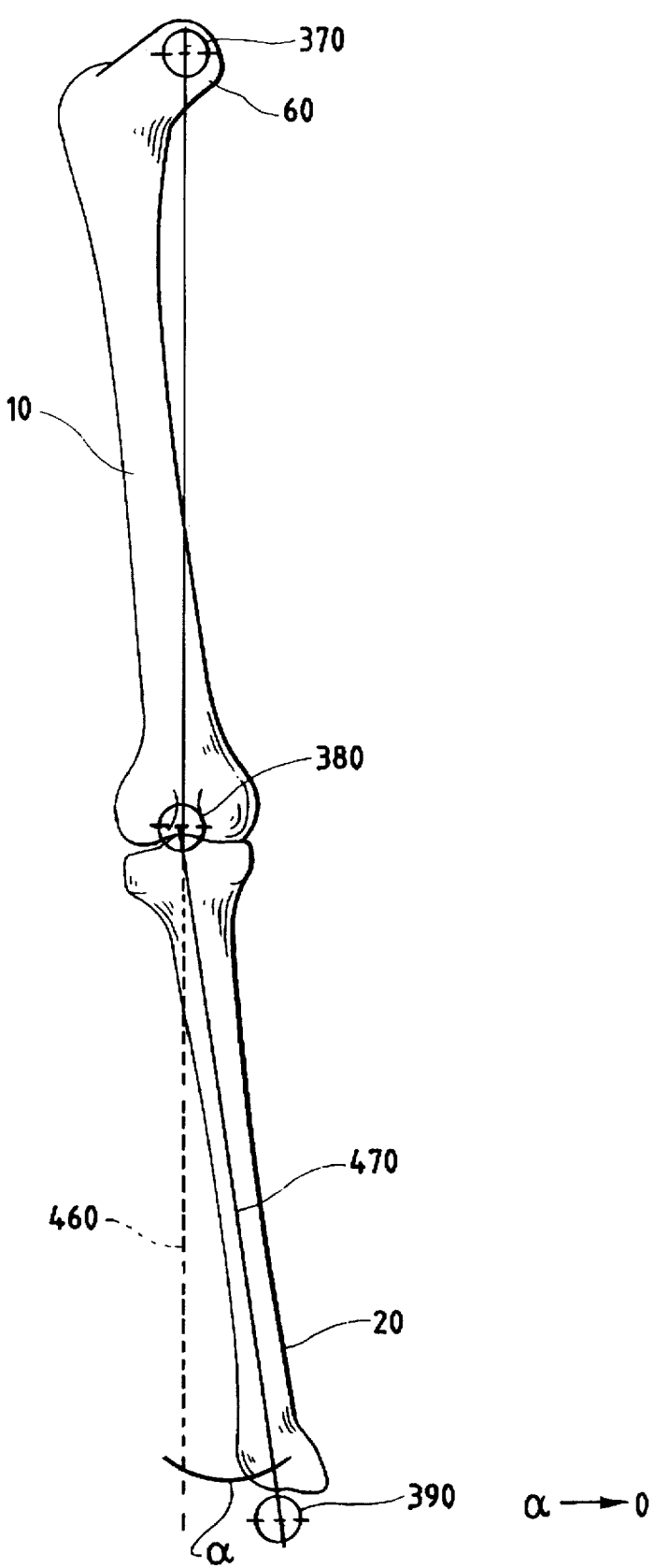
FIG. 9 is a plan view of a femur and a tibia, and their mechanical axes.

As next shown in FIGS. 8–9, the planning software identifies the anatomical features relevant to the surgery on the three-dimensional computer model of the body portion. For UKAs, the planning software identifies certain joint centers to determine optimal limb alignment: a hip center 370, a knee center 380, and an ankle center 390. In order to determine the hip center 370, as reflected by block 400, the operator is asked to identify at least four points on the perimeter of the femoral head 60 in the image data, as is reflected by block 410. Preferably, at least one of these points is in a different image slice from the others. These four points are used to define a sphere, as reflected by block 420. The center of this sphere defines the hip center 370, as reflected by block 430. The image data of the femoral head 60, the four points, and the sphere defined by the four points preferably are displayed on the visual display means 230. In other embodiments, operator interaction may be limited or eliminated entirely, so that the process of defining the hip center 370 is done automatically by planning software programmed to identify four points on the femoral head by locating selected landmarks that uniquely define the anatomical structure.

The steps used to find the knee center 380 are reflected by block 440. The knee center 380 is defined as the mid-point of a line connecting points located approximately at the center of each of the lateral and medial epicondyles of the femur 10 ("epicondyle points"), as reflected by block 443. In one embodiment, the operator visually identifies the epicondyle points directly on a CT image slice, as reflected by block 447, but an automated procedure for determining the knee center 380 in the three-dimensional computer model of the anatomy also could be used. The steps used to find the ankle center 390 are reflected by block 450. The ankle center 390 is determined by finding the midpoint of a line connecting points located approximately at the center of each of the medial and lateral malleoli ("malleoli points"), as reflected by block 453. In one embodiment, the operator visually identifies the malleoli points on an image slice, as reflected by block 457. This procedure also may be automated. The hip center 370, knee center 380, and ankle center 390 preferably are displayed on the visual display means 230.

Figure 10:
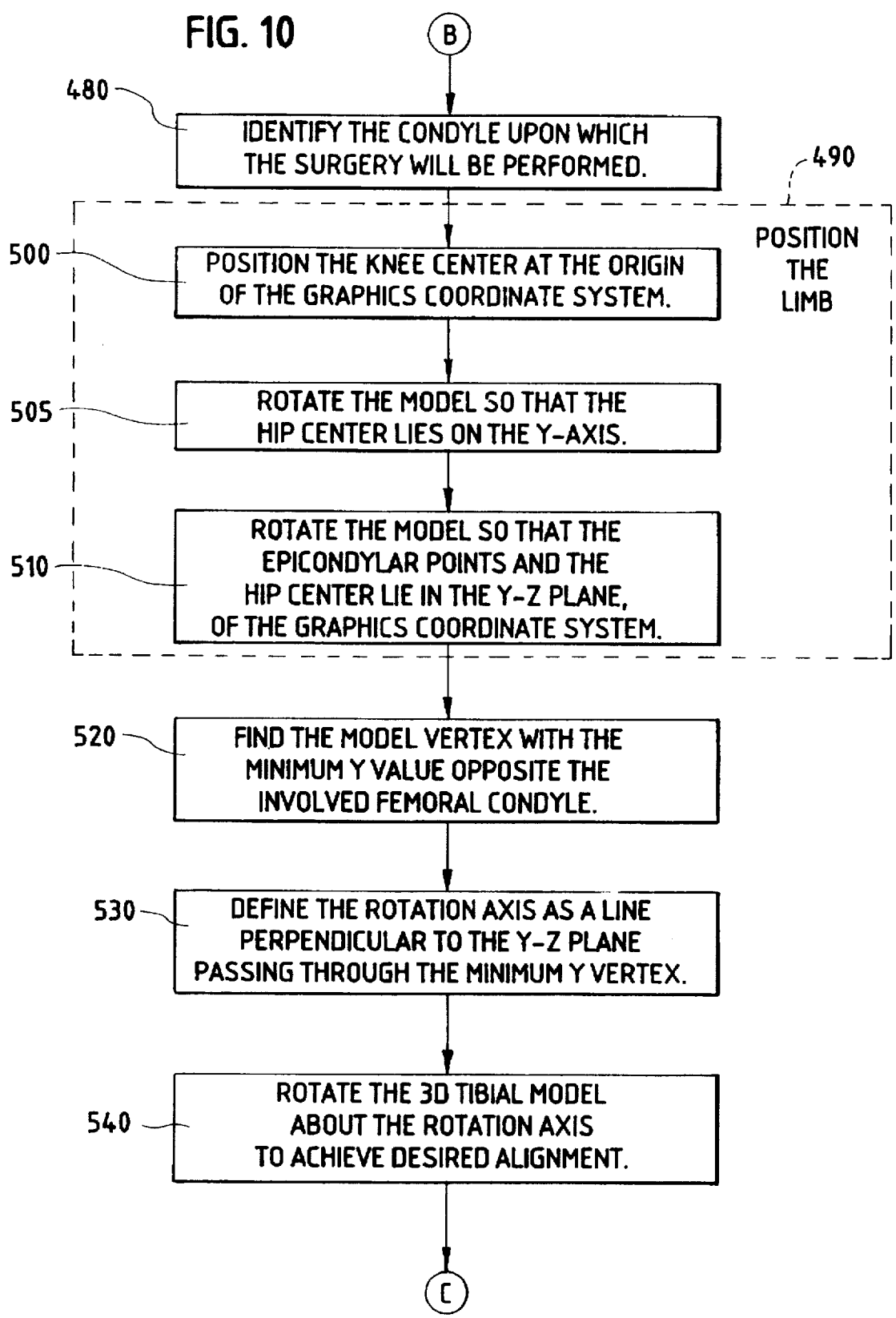
FIG. 10 is a flow chart illustrating one sequence of steps that is useful in the invention to position and align a patient's leg.

Turning now to FIGS. 9–10, the joint center data obtained in the previous step are used to determine the femoral mechanical axis 460 and the tibial mechanical axis 470. The femoral mechanical axis 460 is the line defined by the hip center 370 and knee center 380. Similarly, the tibial mechanical axis 470 is the line defined by the knee center 380 and ankle center 390. The femoral mechanical axis 460 and the tibial mechanical axis 470 preferably are shown on the visual display means 230. The angle α between those axes 460 and 470 in the A/P plane represents the varus/valgus correction needed to correct limb misalignment.

The planning software then uses these axes 460 mad 470 to determine the angular correction needed for proper limb alignment. For determining the desired varus/valgus correction, the operator identifies the condyle upon which the surgery will be performed, as reflected by block 480. Next, the planning software aligns the three-dimensional computer model of the body portion with a graphics coordinate system, as reflected by block 490, by first translating the model so that the knee center 380 lies at the origin of the coordinate system, as reflected by block 500. (The coordinate system is preferably the Cartesian coordinate system; however, other coordinate systems can be used without departing from the instant invention.) The planning software then rotates the model until the hip center 370 lies on a coordinate axis, as reflected by block 505; in one preferred embodiment, the Y-axis is used. The planning software next rotates the model about the selected coordinate axis until a plane formed by the hip center 370 and the epicondyles points lies in the coordinate plane formed using the selected coordinate axes (in the preferred embodiment, the Y-Z plane is used), as reflected by block 510. In this pose, the chosen axis corresponds to the femoral mechanical axis 460, the knee center 380 corresponds to the coordinate system origin, and the A/P plane corresponds to the plane formed by the epicondyles points and the hip center 370. The choices of the axes and the plane are arbitrary, so long as the anatomy is in a known pose within the graphics coordinate system. In the preferred embodiment, the Y-axis was chosen for the mechanical axis because it represents the vertical direction in the Open Inventor Coordinate System designed by Silicon Graphics, Inc., which is a standard coordinate system known in the art for such applications. Other coordinate axes may be chosen without departing from the instant invention.

After alignment is completed, as reflected by block 520, the planning software locates the most-distal point on the condyle opposite the condyle on which the surgery will be performed by finding the vertex on the three-dimensional computer model having the lowest value along the chosen axis on the computer model of the condyle. The planning software then defines a rotation axis as the line perpendicular to the A/P plane that passes through that most distal point, as reflected by block 530. The operator next enters the desired angular alignment and the planning software, as reflected by block 540, rotates the computer model of the tibia about the rotation axis so that the angle α between the femoral and tibial mechanical axes 460 and 470 is equal to the chosen value. In a preferred embodiment of the instant invention, the planning software has a default value (e.g., zero or such other value as desired by the user) for the desired angular correction. In an alternative embodiment of the invention, the planning software determines the desired angular alignment rather than being input by the operator. In another embodiment, a user skilled in the art can choose the point through which the axis of rotation is defined.

Once the proper angular correction has been determined, the system preferably identifies the proper size and/or pose of at least one prosthetic component that will allow the surgeon to implement the correction. The present invention preferably uses the geometry of generic unicompartmental prosthetic components designed to represent the salient features of commercially-available components; other prostheses can be used, however, without departing from the present invention. It is intended that the invention can be used with any commercially-available prosthesis, whether standard or custom-designed, and the structure of the prosthesis is not important except that data representing its size and configuration must be loaded into the planning software in order to provide accurate sizing and placement information and useful planning information.

Figure 11:
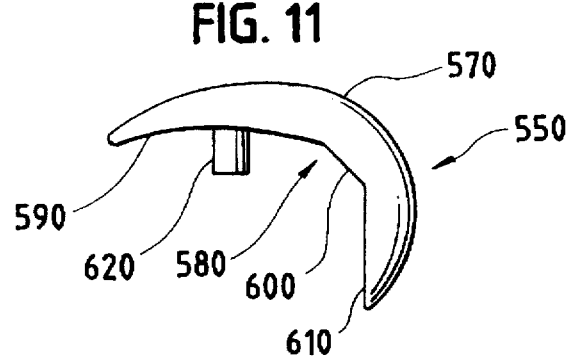
FIG. 11 is a side view of a femoral prosthetic component.
Figure 12:
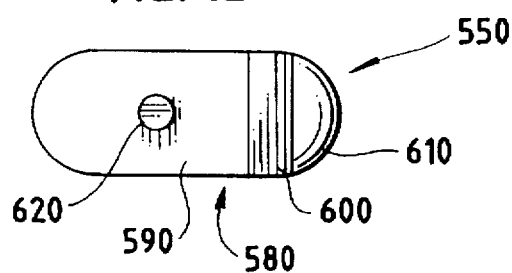
FIG. 12 is a bottom view of a femoral prosthetic component.

As shown in FIGS. 11–14, UKAs employ two prosthetic components: a femoral component 550 and a tibial component 560. As shown in FIGS. 11 and 12, the femoral component 550 has a crescent-shaped profile. The outer, or articular, surface 570 is rounded in both the A/P plane and medial/lateral ("M/L") plane (the plane representing a side view of the body). The inner, or bone contact, surface 580 has three parts; distal 590, chamfer 600 and posterior 610. The distal contact surface 590 is curved in the M/L plane. A cylindrical post 620 extends straight up from the middle of this surface. The chamfer contact surface 600 extends up at an angle from the posterior portion of the distal surface 590 to the posterior contact surface 610, which is parallel to the post 620 on the distal surface 590. Both chamfer 600 and posterior 610 contact surfaces are flat.

Figure 13:
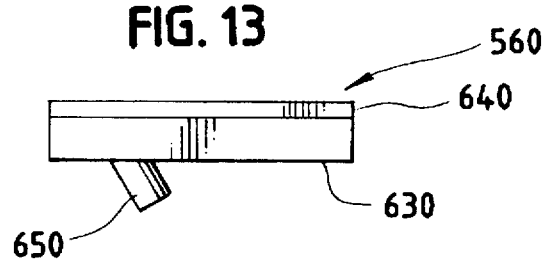
FIG. 13 is a side view of a tibial prosthetic component.
Figure 14:
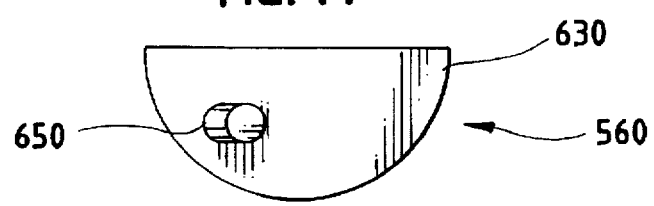
FIG. 14 is a bottom view of a tibial prosthetic component.

Turning to FIG. 13 and 14, the tibial component 560 is a flat, generally semi-circular element consisting of a tibial tray 630 and a tibial articular surface 640. The tibial tray 630, constructed of a bio-compatible metal, has a cylindrical post 650 extending down at an angle from the center of its inferior side. Its superior side has a raised lip around the edges into which the tibial articular surface 640 fits exactly. The tibial articular surface 640, constructed of bio-compatible plastic (e.g., polyethylene), has a concave surface that articulates with the femoral component 550. Other implant designs may be used without departing from the present invention.

Figure 15:
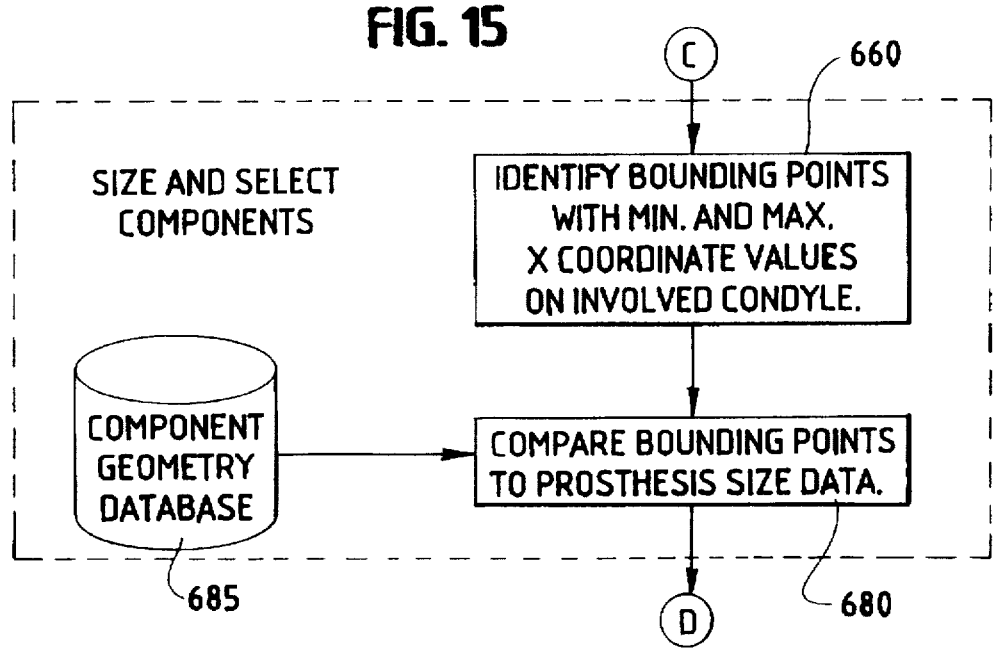
FIG. 15 is a flow chart illustrating one sequence of steps that is useful in the invention to size and select a prosthetic component.

In a preferred method for determining component size, as shown in FIG. 15, either the planning software or the operator identifies the bounding points of the condyle involved in the operation, as reflected by block 660. The bounding points are the most widely-spaced points along the edge of the condyle on an image slice. The image slice used is a slice near where the prosthetic components 550 and 560 will be installed, i.e., near the distal end of the femur 10 and the proximal end of the tibia 20. In an alternative embodiment, the bounding points are identified on an x-ray image, or sampled intraoperatively with a coordinate measuring machine ("CMM") 670 or other measuring device. Once the bounding points are found, as represented in block 680, the planning software compares the bounding points to prosthesis size data, contained preferably in a look-up table located in a component database, as reflected by block 685, stored in a second memory means 690 (which may be the same as the first memory means 220, described above, or different from the first memory means 220) accessible to the computer 210, as shown in FIG. 4, to determine the proper component size. As already noted, this data must be provided for each prosthesis with which the system will be used. In a preferred embodiment, the prosthesis size data includes three-dimensional images of the prosthesis.

In an alternative method for determining component size, the planning computer 210 displays on the visual display means 230 the three-dimensional computer model of the anatomy along with at least two component sizing templates, which are images of the prosthetic components 550 and 560 of different sizes. The operator superimposes each component sizing template on the three-dimensional computer model of the body, and selects the one which fits the three-dimensional computer model of the bone to a degree sufficient to accomplish the desired corrections.

In a less-preferred embodiment, the component size is determined by comparing templates corresponding to the prosthesis with two-dimensional images (e.g., X-rays) of the patient's anatomy. Such techniques are known and used conventionally, or may be used by placing computer equivalents of the templates on computer-displayed facsimiles of the two-dimensional images.

Figure 16:
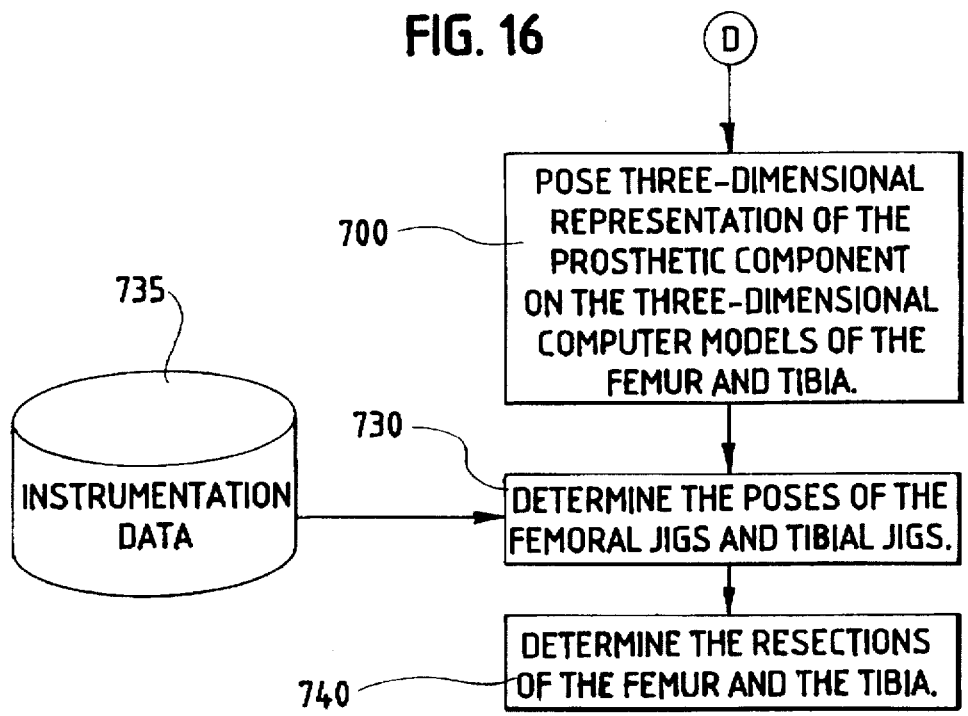
FIG. 16 is a flow chart illustrating one sequence of steps that is useful in the invention to pose a prosthetic component.

Turning now to FIG. 16, the operator next manually poses three-dimensional representations of the prosthetic components 550 and 560 (or, in other words, three-dimensional prosthesis models) on the three-dimensional computer models of the femur 10 and tibia 20, as reflected by block 700. The ability to pose the prosthetic components 550 and 560 preferably is constrained in order to increase the precision and ease of placement. Constraints that, individually or in combination, limit A/P translations, M/L translations and superior/inferior ("S/I") translations (movement up and down the length of the leg, or, in other words, movement perpendicular to the transverse plane), and permit only internal and external rotation (rotation about the mechanical axes of the leg) therefore are desirable. Thus, as a first possible constraint, the femoral and tibial prosthetic components 550 and 560 may be permitted to move only as a pair, rather than individually, and that may be fixed relative to each other in the proper orientation for full knee extension.

A second constraint that may be imposed requires that the inferior surface of the tibial tray 630 be kept perpendicular to the tibial mechanical axis 470. In other words, rotations in the A/P plane and M/L plane are not allowed.

A third constraint that may be imposed requires that A/P translation (movement perpendicular to the A/P plane) and M/L translation (movement perpendicular to the M/L plane) be limited by bounding boxes so that the prosthetic components 550 and 560 cannot be moved outside of the knee. A bounding box is a box formed by the most widely spaced points on the image data. In the instant invention, the bounding boxes are determined by the Silicon Graphics Open Inventor graphics library, but other programs may be used without departing from the instant invention.

A fourth constraint that may be placed on the operator's ability to move the prosthetic components 550 and 560 requires that the surface of each prosthetic component intersect the surface of the corresponding bone, to ensure sufficient contact for fixing the prosthesis to the bone.

A fifth constraint that may be imposed requires that the distal contact surface 590, the chamfer contact surface 600, and the posterior contact surface 610 of the femoral component 550 be at a constant maximum depth relative to the bone surface they will replace. This will ensure equal implant contact throughout the range of motion and prevent the ligaments from being too tight in extension.

Once the operator determines the optimal prosthetic component placement, the planning software determines the poses of the femoral and tibial cutting jigs, as reflected by block 730. Each prosthesis must be used with a corresponding instrumentation set particular to its design, reflected by block 735, so that there is a known relationship between the instrumentation and the prosthesis. Like prosthesis data, instrumentation data must be loaded into the planning software (e.g., from a database) to permit proper placement of the instrumentation, which enables precise resecting of the bones. The poses of instruments are related uniquely to the pose of the prosthesis so that once the prosthesis is placed on the bone in the three-dimensional computer body model, the placement of the instruments may be determined. From the placement of these instruments, the software determines the resections of the femur 10 and the tibia 20, as reflected by block 740. In one embodiment, the resections are reflected by relation to the three-dimensional computer model of the femur 10 and the tibia 20, and displayed on the visual display means 230.

Figure 17:
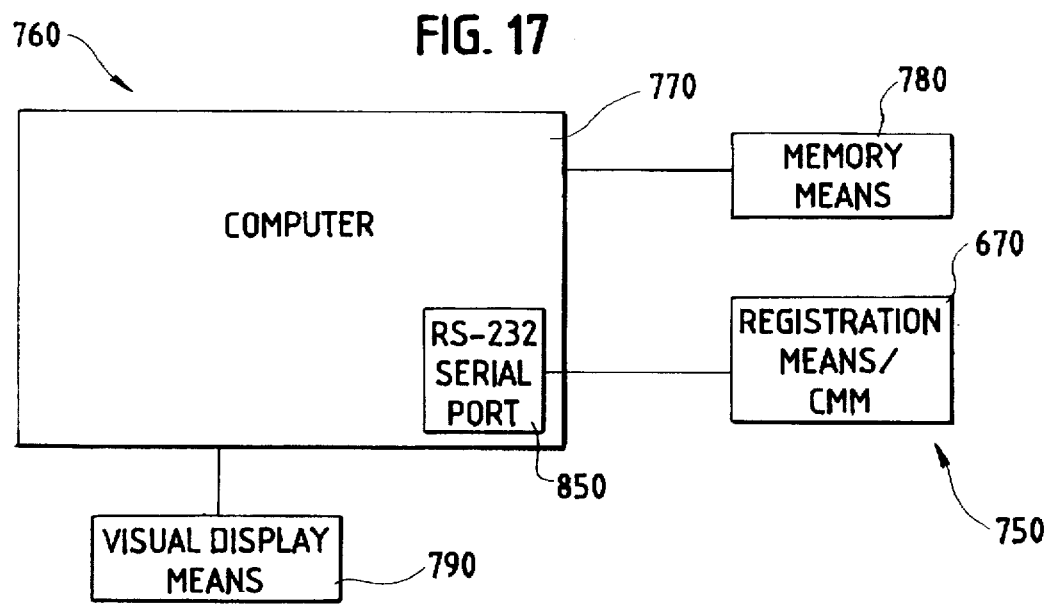
FIG. 17 is a functional block diagram of the procedure computer and associated hardware used in the invention.

In addition to a preoperative planning subsystem, the invention preferably also combines a surgical procedure subsystem. The surgical procedure subsystem allows the surgeon to implement the preoperative plan by accurately guiding the placement of the jigs on the patient's bones. The procedure subsystem, as shown in FIG. 17, first consists of a registration means 750, for registering the three-dimensional computer model of the body to the patient's femur 10 and tibia 20, connected to a procedure workstation 760, which is a computer 770 interfaced to a memory means 780 for storing image data. The memory means 780 is of any suitable form, such as electronic media, electronically erasable media, electromagnetic media, magnetic media, optical media, or magnetic-optical media. The computer 770 further has a visual display means 790 for visually displaying images generated in at least one process step, but preferably displays image generated in more than one process steps. The visual display memos 790 is preferably a raster display means, but other visual display means 790 (such as vector display means) may be used without departing from the instant invention. The registration means 750 is a device that reports to the computer 770 the three-dimensional pose of a movable probe. Suitable registration means 750 include magnetic devices, acoustic devices, mechanical devices (such as a robot arm), or optical devices (such as a wand with LEDs that are sensed by external cameras). The registration means 750 also may be automated. One such embodiment uses a MR imaging machine that images the body portion on which the surgeon is operating and the instruments used in the operation several times a second, thereby providing the surgeon a real-time image of the body portion and the instruments. The MR imaging machine also automatically collects data points, and uses those points instead of manually collected data points to register the body portion and the instruments to the three-dimensional computer model.

Figure 18:
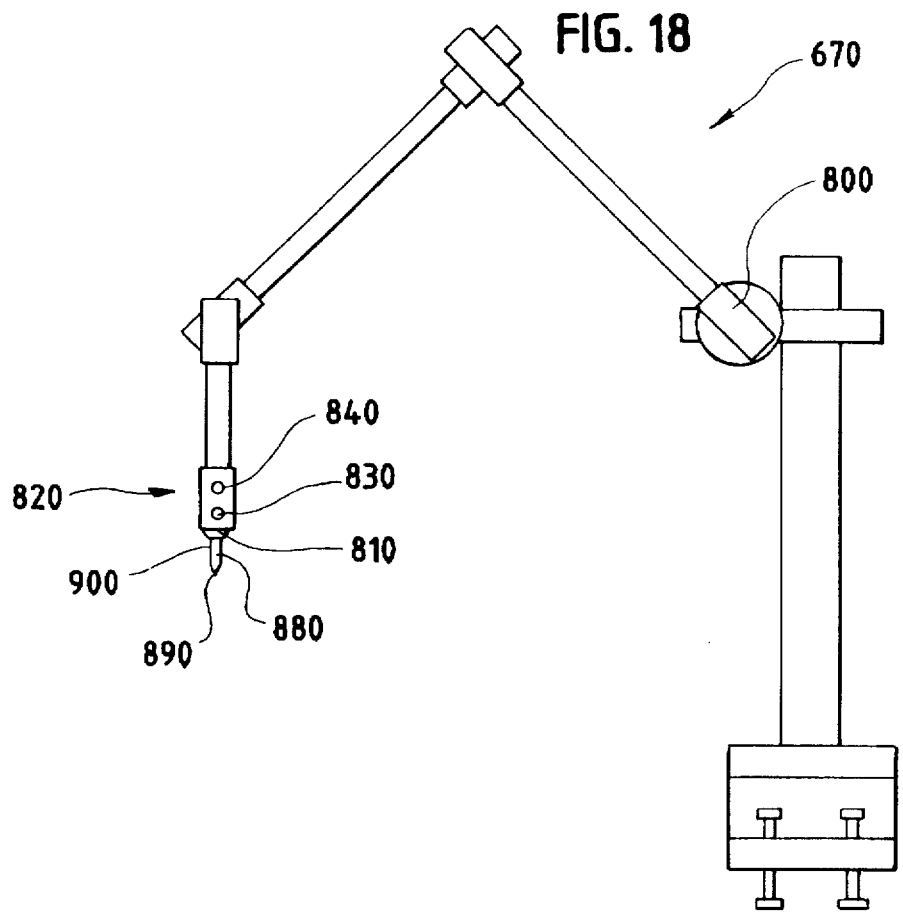
FIG. 18 is a side view of a coordinate measuring machine and a pointer useful in the invention.

In a preferred embodiment, the registration means 750 is a CMM 670 that provides to the computer 770 data regarding the pose of a portion of the CMM 670 relative to a fixed set of spatial coordinates. The CMM 670 must have at least three degrees of freedom; however, in the preferred embodiment, the CMM 670 is a six-degree-of-freedom mechanical arm with six joints and three link members. As shown in FIG. 18, the CMM 670 has a fixed end 800 and a free end 810. The CMM 670 includes at least one input device 820, such as a button, to signal the computer 770. In a preferred embodiment, however, the CMM 670 contains two buttons: a distal button 830 and a proximal button 840, to provide for multiple inputs without the need to release the CMM 670. The preferred CMM 670 is a Faro Metretom CMM; however, other CMMs can be used without departing from the present invention.

The instant invention preferably uses the same computer made for the procedure subsystem as for the planning subsystem; however, other computers may be used without departing from the instant invention. In one embodiment, the computer 770 communicates with the CMM 670 through a standard RS-232 serial port 850; however, other methods of communication can be used without departing from the instant invention.

Figure 19:
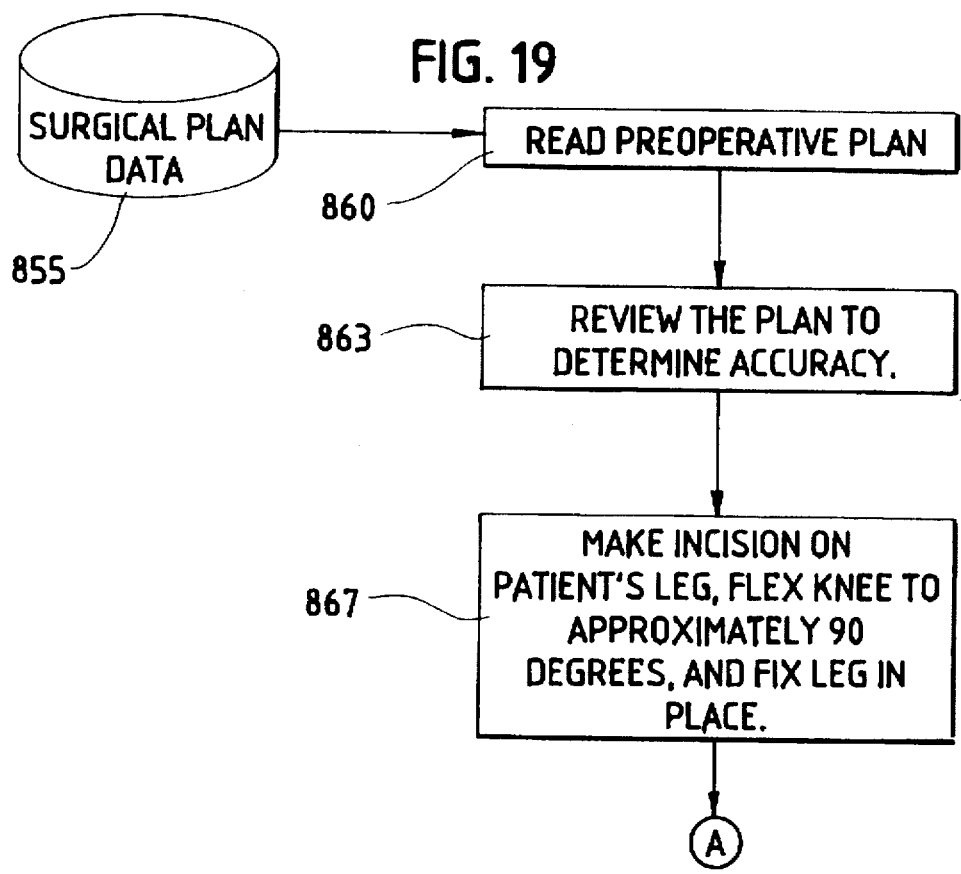
FIG. 19 is a flow chart illustrating one sequence of steps that is useful in the invention to prepare the patient's leg for surgery.

Turning now to FIG. 19, in the procedure subsystem, the memory means 780 containing the surgical plan data, reflected by block 855, is interfaced to the computer 770 and the data is loaded into the procedure software, as reflected by block 860. The surgical plan data preferably is created by the planning software, but it may be created by other means (including manually, or by other planning systems). Preferably, the surgical plan data comprises a three-dimensional computer model of the femur 10 and tibia 20 or the surfaces thereof relevant to the surgery, and data relating to at least one femoral prosthetic component 550 of defined size and pose relative to the femur 10 and at least one tibial prosthetic component 560 of defined size and pose relative to the tibia 20. The surgeon preferably reviews the plan to determine its accuracy, as reflected by block 863. Once the surgeon approves the plan, an incision is made on the patient's leg, as reflected by block 867. The knee is flexed to approximately 90 degrees and fixed in place with any conventional means for holding the leg. In one embodiment, the means for holding the leg is a leg holder consisting of a track mounted on a table with a slidable moving boot placed within the track. The boot is shaped so that it covers the back half of the patient's foot. The patient's foot is fixed into the boot and firmly strapped into place with either tape or bandages. The boot can move within the track in order to flex the knee, but also may be locked into place during surgery if so desired. Other means for holding the leg that allow the leg to be selectively moved or locked into place may be used without departing from the instant invention.

Figure 20:
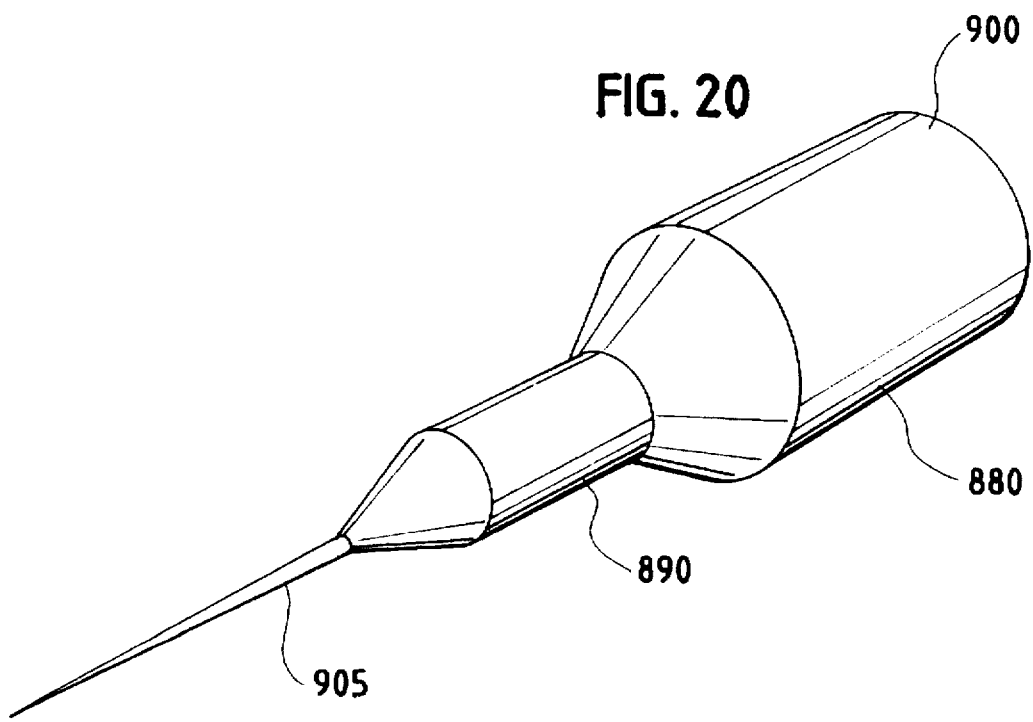
FIG. 20 is a perspective view of a pointer and a transdermal means for registering points underneath a patient's skin useful in the invention.

Once the leg is fixed in place, the femur 10 is registered. As discussed above, registration is the process of defining a geometric transform between the physical world and the three-dimensional computer model. During the registration process, data points are sampled by touching a pointer 870 attached to the CMM 670 to desired points on the patient's bone and signalling the computer 770 of the location of the CMM 670. In the current embodiment, the user signals the computer 770 by pressing a button 820 on the CMM 670, however, other signalling means may be used without departing from the instant invention. In the current embodiment, as shown in FIGS. 18 and 20, the pointer 870 has a cylindrical body 880 with a cone-shaped tip 890 at one end and a second end 900 that attaches to the free end 810 of the CMM 670. In the preferred embodiment, the pointer is removably attached to the CMM. In an alternative embodiment, a transdermal means 905 for registering points through the patient's skin without incision is attached to the free end 810 of the CMM 670. This transdermal means includes a percutaneous means, such as a needle, for registering points through the patient's skin, or may include an ultrasound or other device for probing the anatomy without incision.

Figure 21:
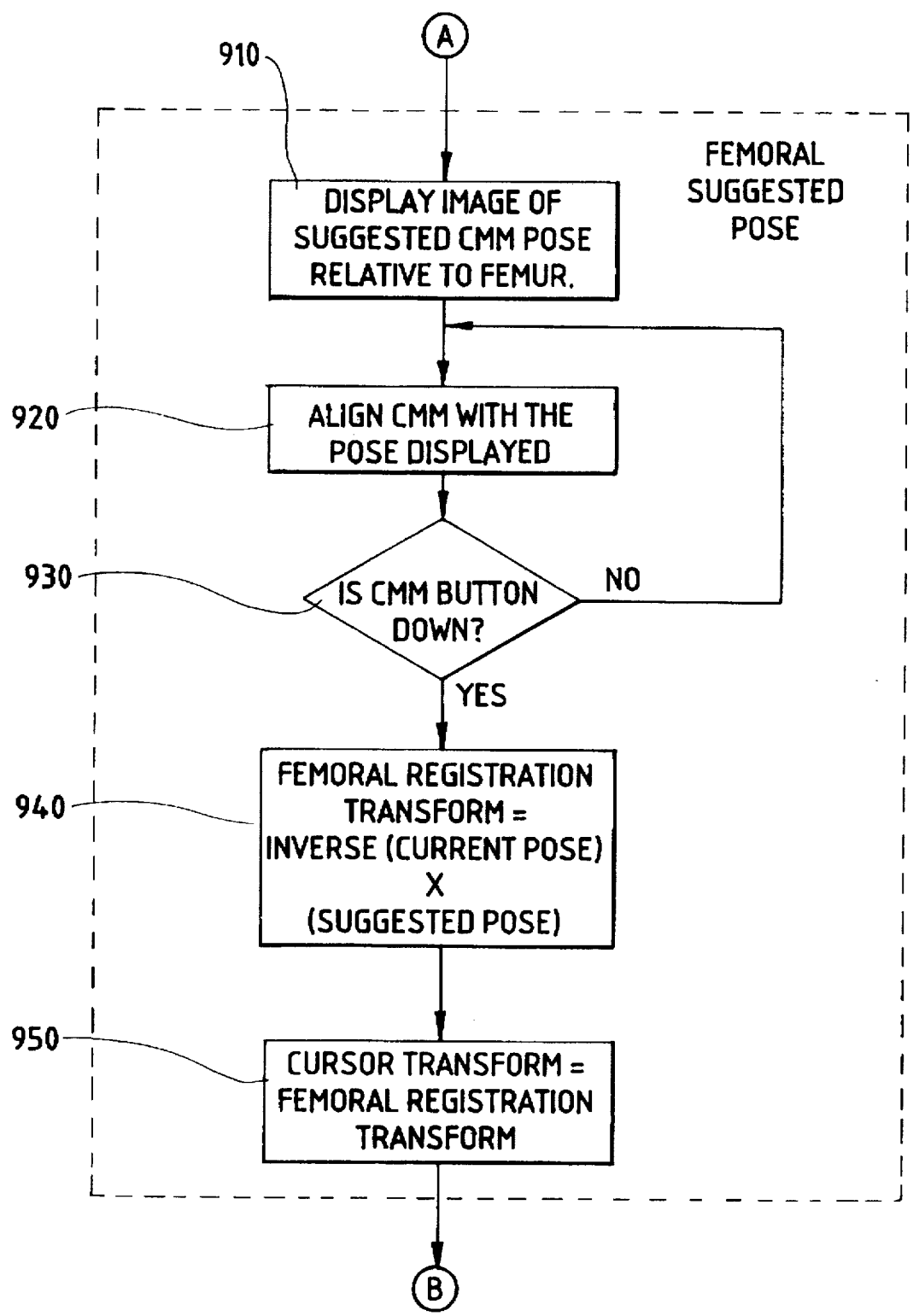
FIG. 21 is a flow chart illustrating one sequence of steps that is useful in the invention to register a femur to a computer model using suggested pose registration.

Registration is a two-part process, beginning with a suggested pose registration and followed by a multi-point optimization. Suggested pose registration is used to define the approximate pose of the patient's bone. The procedure software contains predefined CMM poses relative to each bone. Turning now to FIG. 21, these poses are displayed, as reflected by block 910, and the surgeon is prompted to register the pose by aligning the CMM 670 with the pose displayed, as reflected by block 920, and signalling the computer 770 that the CMM 670 is in the displayed pose by pressing a signalling button 820 on the CMM 670, as reflected by block 930. By relating the predefined pose with the sampled pose, the procedure software can compute a rough registration transform, as reflected by block 940. For registration of the femur, the tip 890 of the pointer 870 is placed at the center of the condyle involved in the operation. The CMM 670 is then pointed parallel to the long axis of the femur 10, while the buttons 830 and 840 on the CMM 670 face anteriorly.

After suggested pose registration is complete, the computer preferably provides visual feedback on the visual display means 790 to inform the user of the accuracy of the registration. In the preferred embodiment, as reflected by block 950, a three-dimensional cursor is displayed on the visual display means 790. The surgeon roughly tests the success of the suggested pose registration by moving the pointer 870 around the surface of the femur 10. The suggested pose registration is adequate if the cursor does not significantly deviate from the surface of the three-dimensional computer model of the femur 10 as the pointer 870 moves about the surface of the femur 10. In practice, it is nearly impossible to achieve an exact match because this process is entirely dependent on the accuracy of the surgeon's estimations of the proper location of the CMM 670, and is therefore subject to human error. However, this approach can give a very good first approximation. Other methods of initial registration may be used that also give a good first approximation of registration, without departing from the instant invention.

Figure 22:
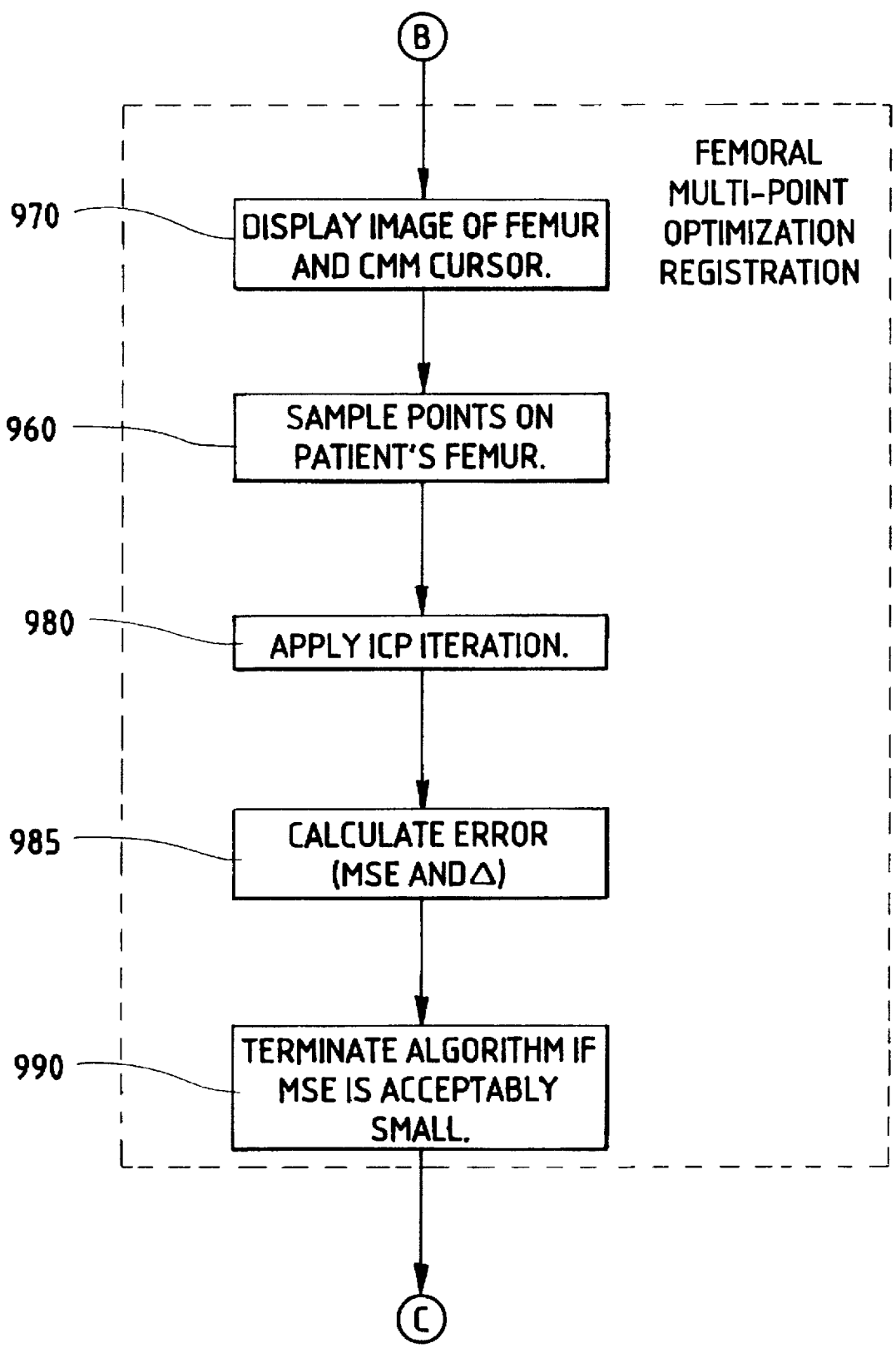
FIG. 22 is a flow chart illustrating one sequence of steps that is useful in the invention to register a femur to a computer model using multi-point optimization registration.

Preferably, as shown in FIG. 22, the multi-point optimization process now is used to define the registration more accurately. First, as reflected by block 960, the surgeon, using the CMM 670, samples a number of points on the surface of the patient's femur 10 that are contained upon a surface of the three-dimensional computer model of the femur 10 that is displayed on the visual display means 790, as reflected by block 970. These points may be sampled from exposed bone, or percutaneously using the transdermal means 905. In a preferred embodiment, the user samples ten points; however, any number large enough to run an accurate optimization algorithm (such as that described by Besl and McKay and known as the Iterative Closest Point algorithm) can be used without departing from the present invention. As the points are sampled, a counter preferably is displayed on the computer indicating the number of points left to sample. If the surgeon errs, such as sampling a point off of the bone surface, the point preferably can be "erased" by pressing a signalling button 820 on the CMM 670. A spurious point also may be identified and deleted automatically by the procedure software, and eliminated from the multi-point optimization. The sampled points preferably are displayed on the visual display means 790.

After sampling, the procedure software relates the sampled points to points on the three-dimensional computer model of the body, to more accurately register the surgical plan data to the femur 10. In the preferred embodiment, as reflected by block 980, the planning software runs an optimization algorithm, which preferably is the Iterative Closest Point algorithm described in Besl, P. J. & McKay, N. D., "A Method for Registration of 3-D Shapes," IEEE Transactions on Pattern Analysis and Machine Intelligence, 14(2), pp. 239–256 (1992). In this algorithm, for each sampled point in a set S, the algorithm computes the distance to the surface of the three-dimensional computer model to create the set M, of the closest surface points. Next, a rotation R, and translation T, are found that minimize the mean square objective function, as reflected by block 985:

$$f(R,T) = \frac{1}{N_S} \sum_{i=1}^{N_S} \|M_i(RS_i + T)\|^2$$

where Ns is the number of points in the set S. Then, the transformation R and T are applied to the sampled points, creating the set S'. If the change in mean square error is below some threshold, t, the algorithm terminates, as reflected by block 990. Otherwise it returns to the first step using the set S'. Other optimization algorithms may be used without departing from the instant invention.

The next step is to register the tibia 20. Tibial registration proceeds in the same manner as femoral registration; suggested pose registration followed by multi-point optimization. For tibial suggested pose registration, the tip 890 of the pointer 870 touches the center of the anterior edge of the tibial plateau 130. The CMM 670 is pointed within the plane of the tibial plateau 130 at the tibial spine 160. The buttons 830 and 840 on the CMM 670 are directed superiorly.

Other registration methods may be used without departing from the instant invention. One such method is fiducial-based registration, in which fiducials are placed in or on the patient's anatomy prior to imaging. Fiducials may be pins of appropriate size inserted into the patient's bones, or radio-opaque stickers attached to external anatomy. After the patient's anatomy has been imaged, the fiducials are located in the image data, and their poses recorded. During the surgery, the CMM 670 is used to locate the poses of the actual fiducials. At least three fiducials are required to completely define the pose of the patient's anatomy with respect to the computer model. Although, as noted above, an advantage of the invention is the ability to use pinless registration, the use of fiducials is not outside the scope of the invention.

Another embodiment uses a registration method in which at least three fiducials or anatomical landmarks are located on multiple two-dimensional images, such as X-rays, and correlated with respect to each other using well-known techniques to define a three-dimensional coordinate system. Still another registration method that may be used with the instant invention is contour matching (also known as curve-matching) registration. In contour matching registration, the operator samples a number of points from characteristic curves on the patient's anatomy using the CMM. Characteristic curves are curves that define the major shape of a surface. For example, one set of curves that may be used for the femur are curves over the sides and top of one of the condyles; however, other curves can be used without departing from the instant invention. A set of curves that may be used for the tibia are curves over the front of the tibial plateau and over the tibial tuberosity; however, again, other curves can be used without departing from the instant invention. In a preferred embodiment, ten to twenty points are sampled per curve; however, any number sufficient to define the shape of the curve may be used without departing from the instant invention. Polynomials or other mathematical functions are next fit to these data points to make smooth curves. These curves then are compared to curvature data obtained from the image data. The procedure software next refines the pose of the curves to better fit the curvature data by matching the curves in the image data to curves sampled from the patient. The process of matching curvature data to refine the pose is part of an iterative process similar to the multi-point optimization process described earlier. Iteration continues until the error falls below some threshold. This registration method requires the construction of a three-dimensional model of the surface being sampled for the purpose of comparing and correlating the sampled points with the computer model.

Following registration the CMM 670 is used to guide the femoral jigs, shown in FIGS. 23–26, into place on the surface of the patient's femur 10. Femoral resection employs the use of at least one femoral jig of defined size and pose relative to the femur 10, and having a defined relationship to the femoral prosthetic component 550 identified in the surgical plan data. In the preferred embodiment, femoral resection employs a femoral jig assembly consisting of a femoral contouring jig 1000 into which fits a femoral docking jig 1010. The docking jig 1010 preferably has a body 1020 shaped like a long box, with a flat front face 1030 to guide a long burr when making the femoral posterior cut. The docking jig 1010 also has a first aperture 1040 extending through the body 1020 to guide the drilling or burring of a post hole and for receiving a positioning device, which is the CMM 670 in the preferred embodiment. The docking jig 1010 further has two horizontal pin holes 1050 and 1060 that are used to attach it to the femoral contouring jig 1000 and both jigs to the CMM 670.

The contouring jig 1000 has a second aperture 1070 into which the docking jig 1010 fits exactly, and at least one surface for guiding a device used to resect the femur 10 (preferably a drill, saw and/or burr). In the preferred embodiment, the contouring jig 1000 has a curved top surface 1080 and an angled base 1090 that extends down from the top surface 1080 at an angle. The top surface 1080 is the distal cut guide surface, which guides a distal resection. The angled base 1090 is the chamfer cut guide surface, which guides a chamfer resection. The contouring jig 1000 has three pin outriggers, one in back 1100 and one on either side 1110 and 1120, through which pins may be placed in order to secure the contouring jig 1000 to the bone. The contouring jig 1000 further has four pin holes (only two of which are shown at 1130 and 1140) drilled horizontally through its body 1150, two on each side, which match the pin holes 1050 and 1060 in the docking jig 1010. In the preferred embodiment, the femoral jigs are made of stainless steel. However, any metal that may be sterilized, is rigid, and is not easily abraded, may be used.

Figure 27:
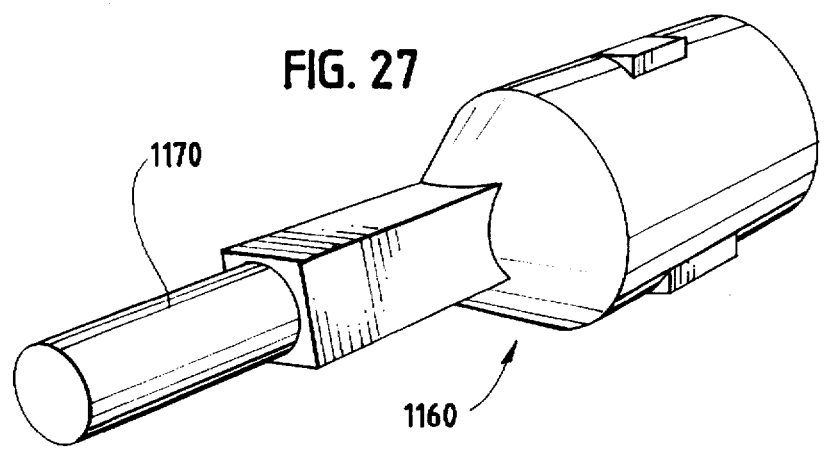
FIG. 27 is a perspective view of a CMM tool mount useful in the invention.

As shown in FIG. 27, in the preferred embodiment, to attach the femoral jigs to the CMM 670, the surgeon removes the pointer 870 from the CMM 670 and replaces it with a CMM tool mount 1160. The CMM tool mount 1160 has a tip 1170 that fits into the first aperture 1040 of the docking jig 1010, and is removably attached to the free end 800 of the CMM 670. The CMM tool mount 1160 also has a pin hole corresponding to the pin hole 1060 on the docking jig 1010. Once the tool mount 1160 is attached to the CMM 670, the user attaches the docking jig 1010 and contouring jig 1000 to the tool mount 1160 by placing the tip 1170 in the first aperture 1040 of the docking jig 1010 and inserting a pin through the vertical holes in all three pieces. Other methods of attaching the femoral jigs to the CMM 670, such as magnetic coupling, vacuum coupling, pneumatic coupling, spring-loaded mechanical coupling, screws or bolts, may be used without departing from the instant invention.

Once the femoral jigs are in place on the CMM 670, the user may guide the femoral jigs into place on the femur 10 and loosely fix them to the bone. In the preferred embodiment, to prepare the femoral jigs for placement, the surgeon applies bone wax or a similar material to an inferior portion 1175 of the docking jig 1010. The wax serves as a loose fixative, aiding the stability of the jigs while they are pinned in place. Other methods of loosely fixing the femoral jigs while they are being pinned in place, such as spikes that temporarily hold the jigs onto the bone, may be used without departing from the instant invention. In another embodiment, a driver is removably attached to the CMM 670. The driver is aligned with and removably attached to the jigs so that the entire assembly can be posed by proper positioning of the CMM 670. Once the proper pose, as directed by the procedure software, is obtained, the driver is used to drive a screw through the femoral jigs into the femur 10 to hold the femoral jigs in place temporarily. After the femoral jigs are pinned into place, the screws are removed. In a similar embodiment, a pin driver, to which the femoral jigs attach, integrated with the CMM 670 is used to temporarily pin the femoral jigs in place. After the femoral jigs are permanently pinned in place, the temporary pins are removed. An alternative embodiment uses a "locking CMM" that has a mechanism that locks the CMM's joints when desired to hold the femoral jigs in place. In yet another embodiment, the arm of the CMM 670 is designed so that motors used to move and pose the CMM 670 can lock the joints in place.

Figure 28:
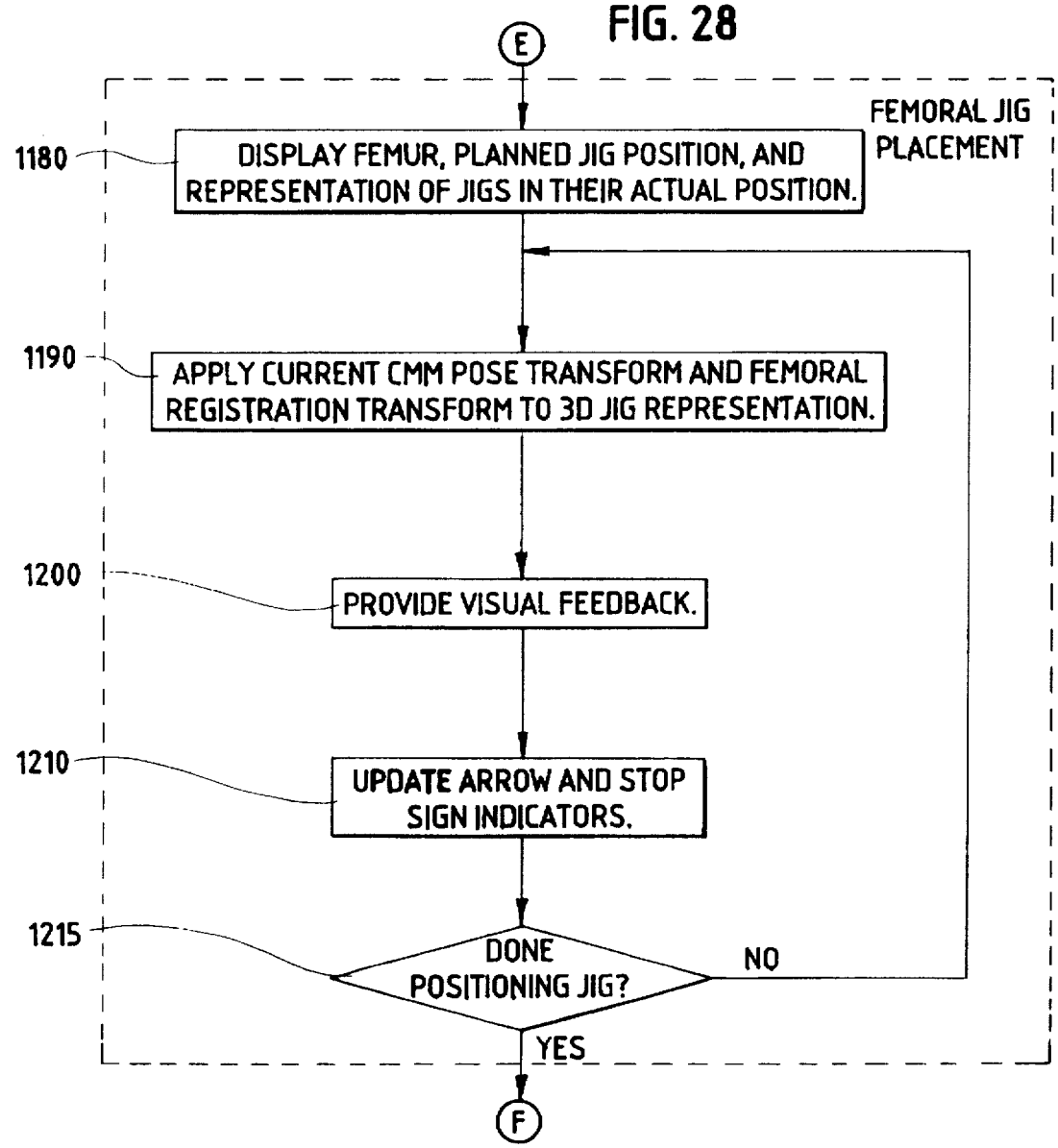
FIG. 28 is a flow chart illustrating one sequence of steps that is useful in the invention to place femoral jigs onto a femur.

Turning to FIG. 28, the surgeon begins jig placement by moving the femoral jigs onto the surface of the femur 10. As reflected by block 1180, a representation of the femoral jigs in both their proper poses on the bone surface and in their actual locations relative to the patient is displayed on the visual display means 790 so that the representation moves in correspondence with the movement of the femoral jigs. The surgeon then aligns the representation of the femoral jigs with the optimal jig placement by moving the CMM 670, as reflected by block 1190. The computer 770 preferably provides visual and/or aural feedback to indicate how close the surgeon is to accurately posing the jigs on the femur 10 according to the surgical plan. In a preferred embodiment, as reflected by block 1200, the computer 770 provides visual feedback by changing the color of the images of the femoral jigs as the femoral jigs are moved closer to their proper pose on the femur 10. In addition, as reflected by block 1210, the computer 770 preferably displays indicators, such as arrows, to indicate the direction of movement or rotation necessary to achieve alignment. When the correct placement has been achieved, a "stop" indicator preferably is displayed.

When the femoral jig assembly is in the correct pose, as reflected by block 1215, it is pinned into place. The surgeon places the pins first by drilling guide holes through the pin holes 1130 and 1140 in the femoral contouring jig 1000. The user then places three surgical pins into the pin holes 1130 and 1140 to anchor the femoral jigs. Steinman surgical pins preferably are used; however, other pins may be used without departing from the instant invention. With the pins in place, the CMM 670 may be removed from the docking jig 1010.

The surgeon now places the tibial jigs onto the tibia 20. Tibial resection employs at least one tibial jig 1220 of defined size and pose relative to the tibia 20, and having a defined relationship relative to the tibial prosthetic component 560 defined in the surgical plan data. In the preferred embodiment, as shown in FIGS. 29 and 30, tibial resection employs the use of a tibial jig 1220 having a flat horizontal surface 1230 and a flat vertical surface 1240 perpendicular to each other to guide a device used to resect the tibia 20 (preferably a long burr bit or saw). The tibial jig 1220 further has a docking hole 1250 for receiving a positioning device, which is the CMM tool mount 1160 attached to the CMM 670 in the preferred embodiment. The tibial jig 1220 also has two peg holes 1260 and 1270 in the horizontal surface 1230. In another embodiment, a tibial post hole guide also is used to resect the tibia. The tibial post hole guide is a tube mounted on a flat surface, through which a long narrow burr or drill is guided to make a post hole in the tibia 20. The tibial post hole guide further has two pegs extending perpendicular to its base, which correspond exactly to the peg holes 1260 and 1270 in the tibial jig 1220 where the tibial post hole guide is seated. The tibial jigs are made of the same material as the femoral jigs.

The tibial jig 1220 is attached to the CMM 670 in the same basic way as the femoral jigs. Preferably, a docking pin is inserted through the aligned holes of the CMM tool mount 1160 and the tibial jig's docking hole 1250; however, other methods of attaching the tibial jigs to the CMM 670 may be used without departing from the instant invention. Preferably, the user then places wax onto the contact surface of the tibial cutting jig 1220; however, other methods of temporarily attaching the tibial jigs to the tibia 20 may be used without departing from the instant invention. The tibial jig 1220 is aligned using the same procedure that was used for the femoral jigs, using visual and aural feedback. The pin holes are drilled and surgical pins are inserted to fix the tibial jig 1220 to the tibia 20. The user then removes the CMM 670.

Turning now to FIG. 31, the patient's knee is now ready for bone resections. Tibial resection is performed in three steps, as reflected by block 1280. The three tibial resections all use a long burr, saw, and/or drill, and proceed in the following order; horizontal and vertical resections followed by creating a post hole by drilling or burring. The horizontal resection is made along the horizontal surface 1230 of the tibial cutting guide 1220 with either a saw or a long burring device. Vertical resection proceeds in the same manner along the vertical surface 1240 of the tibial cutting guide 1220. In an alternative embodiment, the user then places the post hole guide by inserting the pegs on its body into the holes in the horizontal surface 1230 of the tibial cutting guide 1220. The user guides a drill or long burr through the tube to create the post hole.

As reflected by block 1290, femoral resection involves three different cuts. The posterior cut is made first with either a saw or long burr along the front face 1030 of the femoral docking jig 1010. The user then inserts a drill or long burr through the first aperture 1040 to create the post hole. The distal and chamfer resections are made by guiding a collared burr along the distal and chamfer guide surfaces 1080 and 1090 of the contouring jig 1000. The depth of the burring is limited by the contact of the collar with the distal and chamfer guide surfaces 1080 and 1090 of the contouring jig 1000.

Figure 32:
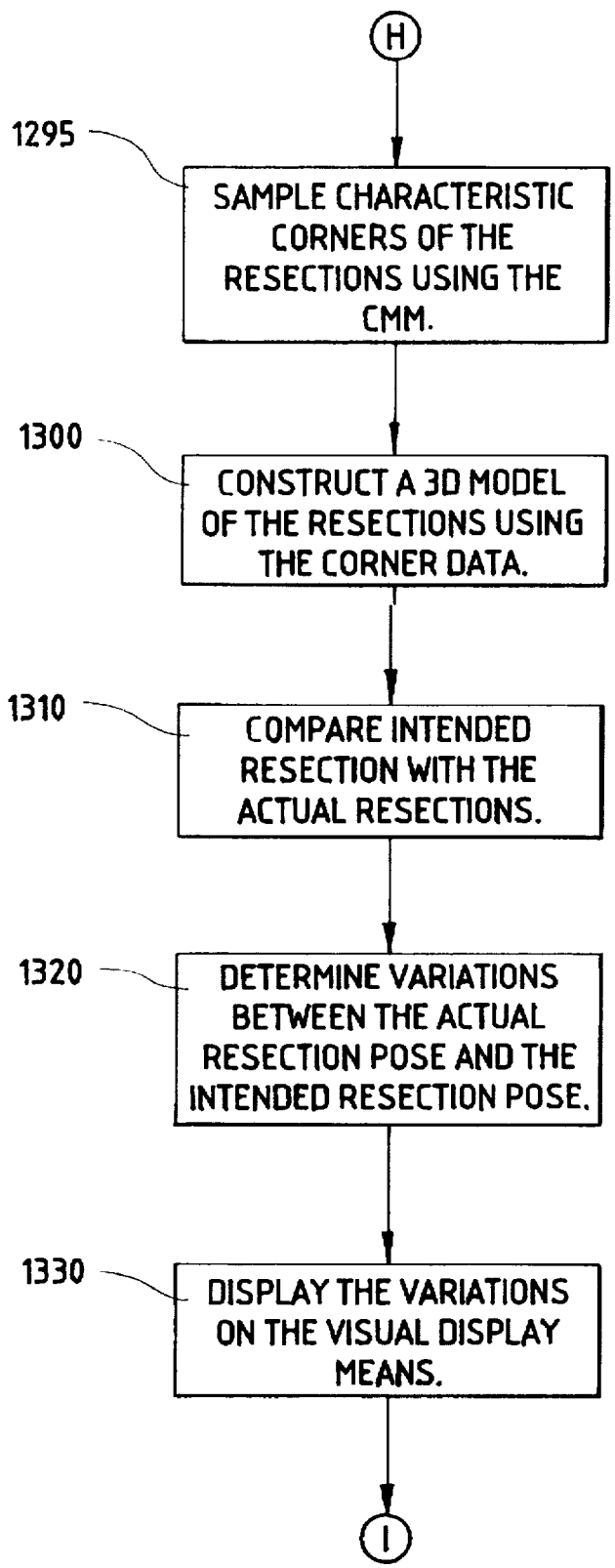
FIG. 32 is a flow chart illustrating one sequence of steps that is useful as an alternative embodiment of the invention to determine how close actual resections are to intended resections.

In the preferred embodiment, as shown in FIG. 32, the surgeon next determines how close the resections are to intended resections that were defined in the surgical plan. First, as reflected by block 1295, the surgeon uses the CMM 670 to sample characteristic corners of the resections; for the femoral resections, these corners are the medial and lateral corners of the chamfer/distal resections interface, and the medial and lateral corners of the chamfer/posterior cut interface; for the tibial resections, the characteristic corners are the anterior and posterior corners of the horizontal/ vertical cut interface. The procedure software uses the characteristic corner data to construct a three-dimensional model the actual femoral and tibial resections, modeling the planes defined by the characteristic corners, as shown by block 1300. (The characteristic corners and the actual resections may be shown on the visual display means 790.) The procedure software compares the intended resections with the actual resections, as reflected by block 1310, and determines whether and to what extent there exist variations between the pose of the actual resections and the pose of the intended resections, as reflected by block 1320. The procedure software then displays these variations on the visual display means 790, as reflected by block 1330.

Figure 33:
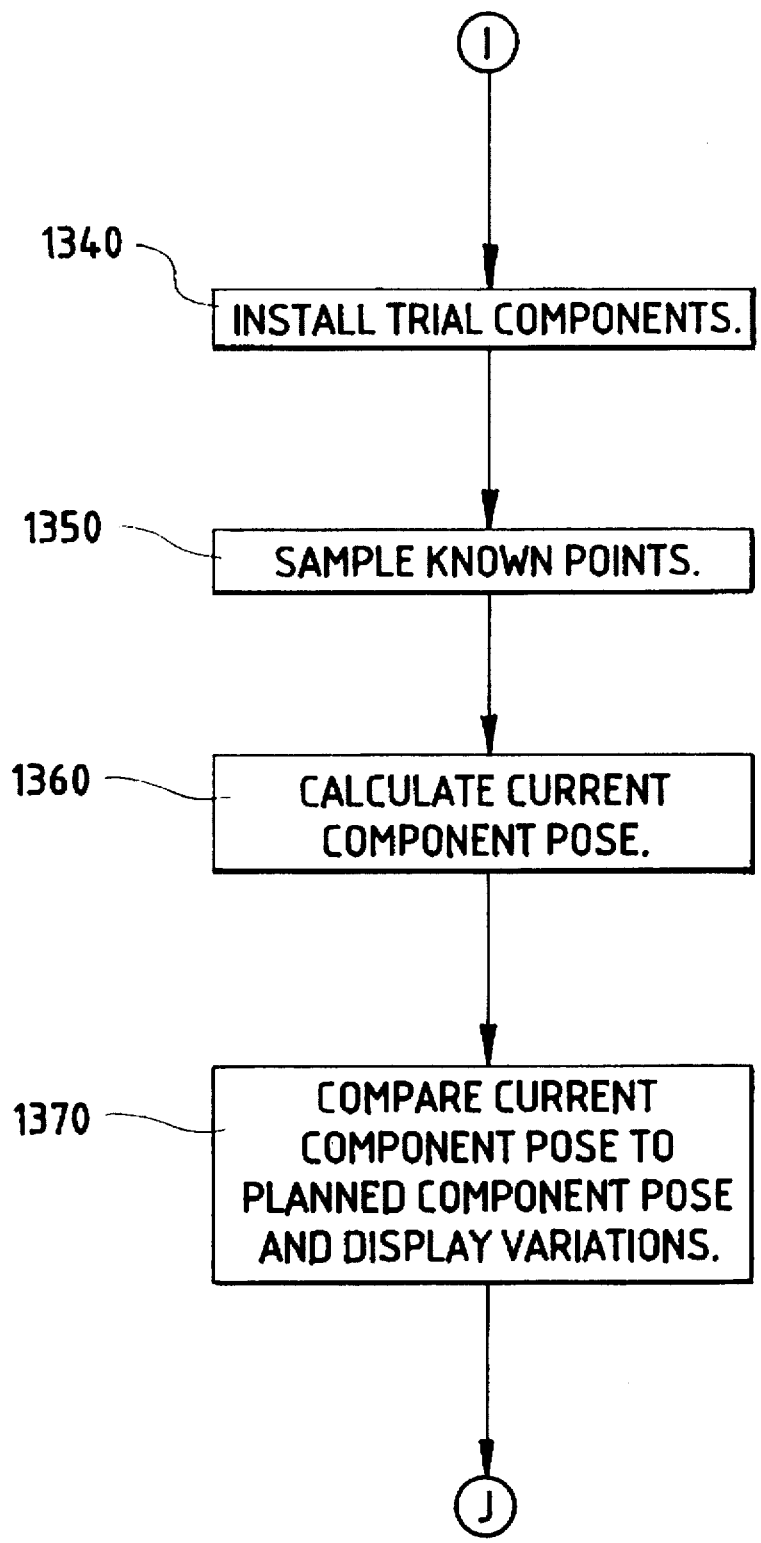
FIG. 33 is a flow chart illustrating one sequence of steps that is useful as an alternative embodiment of the invention to determine placement error of a prosthetic component.

Turning now to FIG. 33, in the preferred embodiment, the procedure software also permits the surgeon to compare the intended placement of the prosthesis, as defined in the surgical plan, with the actual placement of the prosthesis as represented by trial components. As reflected by block 1340, the surgeon installs trial components that each have three or more known points defined on their surfaces (i.e., the three-dimensional locations of the points relative to the geometry of the prosthetic components are located in the procedure software). The surgeon then samples these points using the CMM 670, as reflected by block 1350. Next, as reflected by block 1360, the procedure software determines the pose of the actual femoral and tibial trial components from the sampled points. The procedure software then, as reflected by block 1370, compares the actual pose of the femoral and tibial prosthetic trial components with the intended pose of femoral and tibial prosthetic components 550 and 560, and determines whether and to what extent there are variations. The procedure software then displays these variations on the visual display means 790.

Figure 34:
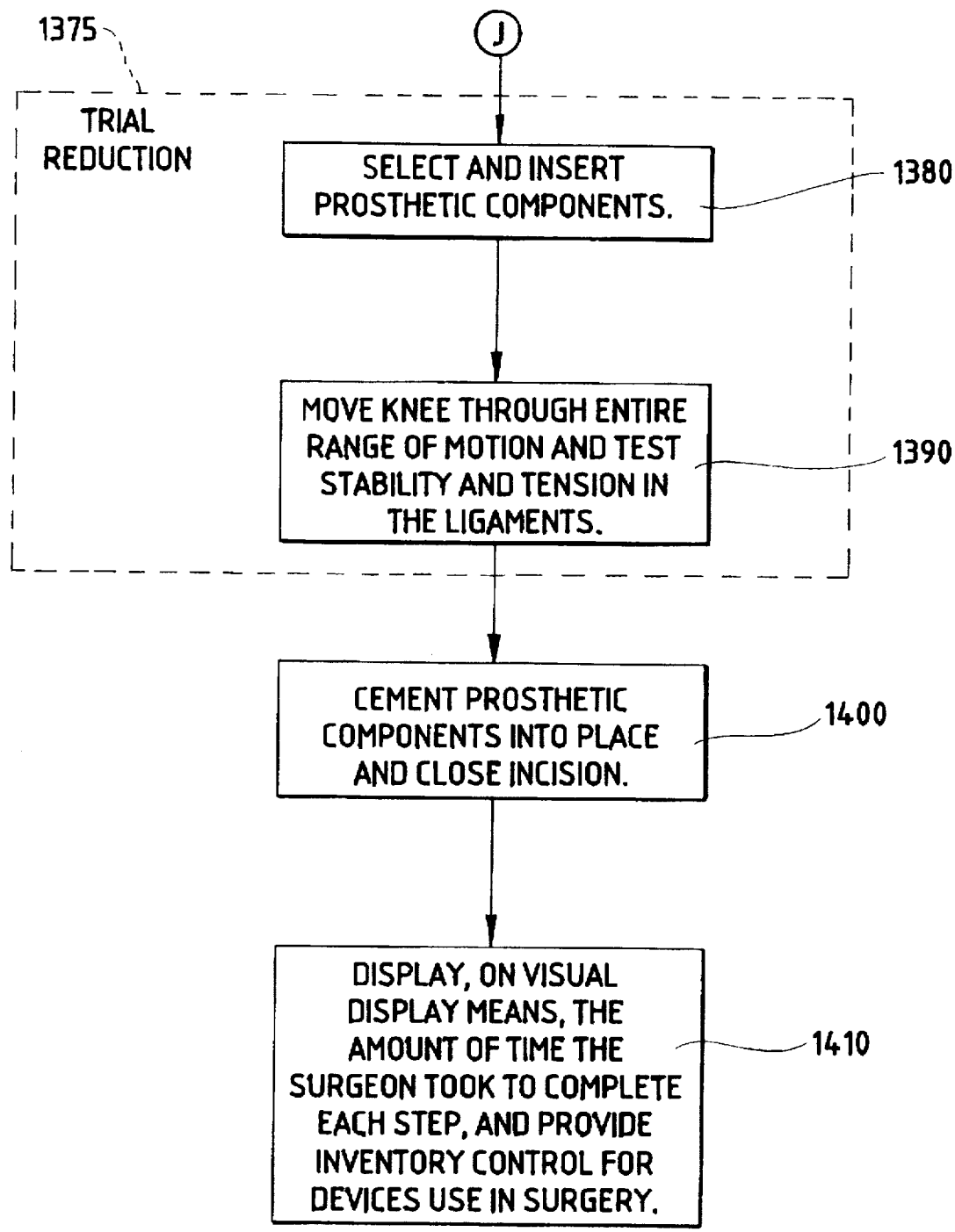
FIG. 34 is a flow chart illustrating one sequence of steps that is useful as an alternative embodiment of the invention to perform a trial reduction, to cement prosthetic components into place, to close an incision, to display the amount of time a surgeon took to complete the process steps, and to provide an inventory control for devices used in surgery.

Turning now to FIG. 34, the next step is a trial reduction, as reflected by block 1375. The surgeon first selects the prosthetic components 550 and 560 recommended during the planning stage, as reflected by block 1380. The prosthetic components 550 and 560 then are inserted. The knee, with the prosthetic components 550 and 560 in place, is moved through its entire range of motion, and the stability and tension in the ligaments is tested, as reflected by block 1390. The thickness of the tibial articular surface 640 should be such that a maximal area of contact between the femoral articular surface 570 and tibial articular surface 640 exists, while not prohibiting a full range of motion.

Once the trial reduction is completed, and the surgeon is satisfied that the prosthetic components 550 and 560 properly fit, the prosthetic components 550 and 560 are cemented into place, and the incision closed in the usual manner, as reflected by block 1400. After the surgery is complete, the procedure computer 770 preferably displays on the visual display means 790 the amount of time the surgeon took to complete each step, and also may provide an inventory control for devices used during surgery, as reflected by block 1410.

The invention has several advantages over current mechanical instrumentation systems, surgical planning systems and computer-assisted surgical systems.

Mechanical instrumentation systems in use today rely on cutting jigs that align cuts using discrete metrics and visual means, which can introduce alignment errors. In addition, these systems require a large surgical exposure because the instrumentation is large, even for current UKA systems. The instrumentation is large because it needs to cover certain anatomical landmarks in order to align the cutting jigs.

The invention overcomes alignment problems by determining optimal alignment preoperatively and using computer guidance to help the surgeon achieve this alignment. The computer replaces large, complicated mechanical alignment systems, allowing smaller jigs to be used, and thus a smaller incision to be made. A smaller incision will result in a less invasive procedure, and will lead to a shorter rehabilitation time, thereby reducing costs, morbidity, and patient complaints.

Surgical planning systems have been introduced that help plan surgical procedures. Alignment of tools and prosthetic devices in relation to patient anatomy can be planned preoperatively using these systems, but many do not provide a means to implement the plan in the operating room. The invention not only allows detailed planning of a procedure, but also provides a method to implement the surgical plan.

The preoperative planning and intraoperative procedure systems of the instant invention provide also for better limb alignment and more accurate prosthetic component placement. This results in less prosthetic component wear and better prosthetic component fixation than is possible without these systems, thereby leading to longer lasting components requiring fewer revision surgeries, and better post-surgery joint functionality, thereby improving range of motion, knee function, and biomechanical performance. The instant invention also will help reduce revision surgeries.

Current computer-assisted surgical systems allow planning and implementation of a surgical procedure, but they suffer from additional problems. Most are expensive, require a specially trained technician for operation, and use pin-based registration. The invention is expected to be relatively inexpensive and easy-to-use by an orthopaedic surgeon. Also, it uses a shape-based registration algorithum that does not introduce any of the problems associated with pin-based registration, such as increased invasiveness mad pain.

The present invention has been described with respect to one embodiment, which is not meant to and should not be construed to limit the invention. Those skilled in the art will understand that variations from the embodiments and conditions described herein may be made without departing from the invention as claimed in the appended claims.

What is claimed is:

1. A method for planning surgery on a portion of a body with the goals of improving the accuracy of the surgery and reducing the risks associated with surgery, comprising the steps of:

gathering image data of the portion of a body using a radiant energy means for gathering image data;

storing the image data in a memory means for storing image data;

reading the stored image data into a computer interfaced to the memory means, the computer having a visual display means for visually displaying images generated in at least one process step;

generating a three-dimensional computer model of the body portion from the image data using a modeling means for creating three-dimensional computer models from the image data;

identifying anatomical features relevant to the surgery on the three-dimensional computer model of the body portion; and using software to define at least one desired correction to the anatomical structures to be accomplished by the surgery.

2. The method for planning surgery of claim 1, wherein the radiant energy means for gathering image data is selected from a group consisting of magnetic resonance imaging devices, X-ray devices, and computed tomography imaging devices.

3. The method for planning surgery of claim 1, wherein the memory means for storing image data is selected from a group consisting of electronic media, electronically erasable media, electromagnetic media, magnetic media, optical media, and magnetic-optical media.

4. The method for planning surgery of claim 1, wherein the visual display means is selected from a group consisting of raster display means and vector display means.

5. The method of planning surgery of claim 1, wherein the image data represent discrete areas corresponding to at least one relevant anatomical structure, wherein boundaries defining each anatomical structure are determined by predefined variations in the image data, and wherein the modeling means locates the boundaries that define the anatomical structures to create the three-dimensional computer model of the body portion.

6. The method for planning surgery of claim 5, wherein the modeling means locates the boundaries that define the surfaces of the anatomical structures and defines continuous curves corresponding to those boundaries to construct the three-dimensional computer model from those continuous curves.

7. The method of planning surgery of claim 6, wherein the modeling means uses a Canny filter to define a set of edges corresponding to the boundaries that define the surfaces of the anatomical structures.

8. The method for planning surgery of claim 7, wherein the modeling means uses a snake algorithm first to form active contours, and then to adjust the sizes and shapes of the active contours to fit the set of edges.

9. The method of planning surgery of claim 8, wherein the modeling means uses points on the active contours to create surface patches.

10. The method for planning surgery of claim 9, wherein the modeling means uses a third-order polynomial equation to define the surface patches.

11. The method for planning surgery of claim 10, wherein the surface patches are Bezier patches.

12. The method for planning surgery of claim 10, wherein the modeling means tessellates the surface patches into polygonal meshes that in combination correspond to the relevant anatomical structures.

13. The method for planning surgery of claim 1, wherein the modeling means is software.

14. The method for planning surgery of claim 1, wherein the modeling means identifies the relevant anatomical structures.

15. The method for planning surgery of claim 1, wherein the three-dimensional computer model of the body portion is displayed on the visual display means.

16. The method for planning surgery of claim 1, wherein software is used to define the desired corrections.

17. The method for planning surgery of claim 1, wherein the relevant anatomical features are displayed on the visual display means.

18. The method for planning surgery of claim 1, further comprising the step of determining the size and pose of at least one prosthesis to be used in the surgery.

19. The method for planning surgery of claim 18, wherein prothesis size data is stored in a second memory means accessible by the computer, and further comprising the step of determining prosthesis size and pose by comparing the three-dimensional computer model of the body portion with the prothesis size data.

20. The method for planning surgery of claim 19, wherein the prothesis size data includes at least two three-dimensional prosthesis images of different sizes.

21. The method for planning surgery of claim 20, wherein at least two three-dimensional prothesis images of different sizes are displayed on the visual display means, superimposed on the three-dimensional computer model of the body portion, and wherein a three-dimensional prosthesis image of a particular size is chosen to fit the three-dimensional computer model to a degree sufficient to accomplish the defined desired correction.

22. The method for planning surgery of claim 21, wherein at least two three-dimensional prothesis images of different sizes are displayed on the visual display means superimposed on the three-dimensional computer model, and wherein an operator chooses the size of the three-dimensional prosthesis image to fit the three-dimensional computer model of the body portion to a degree sufficient to accomplish the defined desired correction.

23. The method for planning surgery of claim 18, wherein the pose of the three-dimensional prosthesis image is adjusted to fit the three-dimensional computer model of the body portion to a degree sufficient to accomplish file defined desired correction.

24. The method for planning surgery of claim 23, wherein an operator adjusts the pose of the three-dimensional prosthesis image to fit the three-dimensional computer model of the body portion to a degree sufficient to accomplish the defined desired correction.

25. The method for planning surgery of claim 18, wherein the three-dimensional prothesis image is displayed on the visual display means superimposed on the three-dimensional computer model of the body portion, and wherein the size and pose of the three-dimensional prosthesis image are adjusted to fit the three-dimensional computer model to a degree sufficient to accomplish the defined desired correction.

26. The method for planning surgery of claim 25, wherein the three-dimensional prothesis image is displayed on the visual display means superimposed on the three-dimensional computer model of the body portion, and wherein an operator adjusts the size and pose of the three-dimensional prosthesis image of the prosthesis to fit the three-dimensional computer model to a degree sufficient to accomplish the defined desired correction.

27. The method for planning surgery of claim 18, further comprising the step of determining characteristics of at least one resection to be performed on the anatomical structures.

28. The method for planning surgery of claim 27, wherein the resection is shown in relation to the three-dimensional computer model and displayed on the visual display means.

29. A method for planning unicompartmental knee arthroplasty surgery with the goals of improving the accuracy of the surgery and reducing the risks associated with surgery, comprising the steps of:

gathering image data of a femur and a tibia using a radiant energy means for gathering image data;

storing the image data of the femur and tibia in a memory means for storing image data;

reading the stored image data into a computer interfaced to the memory means, the computer having a visual display means for visually displaying images generated in at least one process step;

generating a three-dimensional computer model of the femur and tibia using a modeling means for constructing three-dimensional computer models from the image data;

identifying a hip center on the three-dimensional computer model;

identifying a knee center on the three-dimensional computer model;

identifying an ankle center on the three-dimensional computer model;

defining the line from the hip; center to the knee center on the three-dimensional computer model;

defining the line from the knee center to the ankle center on the three-dimensional computer model;

determining a desired varus/valgus correction on the three-dimensional computer model;

determining the size and pose of both a femoral prosthetic component and a tibial prosthetic component to accomplish the desired correction on the three-dimensional computer model; and, determining the size and pose characteristics of resections to be performed on the femur and the tibia as shown in the computer model.

30. The method for planning surgery of claim 29, wherein the radiant energy means for gathering image data is selected from a group consisting of magnetic resonance imaging devices, X-ray devices, and computed tomography imaging devices.

31. The method for planning surgery of claim 29, wherein the memory means for storing image data is selected from a group consisting of electronic media, electronically erasable media, electromagnetic media, magnetic media, optical media, and magnetic-optical media.

32. The method for planning surgery of claim 29, wherein the visual display means is selected from a group consisting of raster display means and vector display means.

33. The method of planning surgery of claim 29, wherein the image data represents discrete areas corresponding to each of the femur and tibia; wherein boundaries that define surfaces of each of the femur and tibia are determined by predefined variations in the image data; and, wherein the modeling means locates the boundaries that define each of the femur and tibia to create the three-dimensional computer model.

34. The method for planning surgery of claim 32, wherein the modeling means locates the boundaries that define the surfaces of each of the femur and tibia, and defines continuous curves corresponding to those boundaries to construct the three-dimensional computer model from those continuous curves.

35. The method for planning surgery of claim 33, wherein the modeling uses a Canny filter to define a set of edges corresponding to the boundaries that define the surfaces of each of the femur and tibia.

36. The method for planning surgery of claim 35, wherein the modeling means uses a snake algorithm first to form active contours, and then to adjust the sizes and shapes of the active contours to fit the set of edges.

37. The method for planning surgery of claim 36, wherein the modeling means uses points on the active contours to create surface patches.

38. The method for planning a surgery of claim 37, wherein the modeling means uses a third-order polynomial equation to define the surface patches.

39. The method for planning a surgery of claim 38, wherein the surface patches are Bezier patches.

40. The method for planning a surgery of claim 38, wherein the modeling means tessellates the surface patches into polygonal meshes that in combination correspond to surfaces of the femur and tibia.

41. The method for planning a surgery of claim 29, wherein the modeling means is software.

42. The method for planning a surgery of claim 29, wherein the image data of a femur includes data relating to a femoral head having a perimeter, and wherein the step of identifying the hip center comprises identifying at least four points on the perimeter of the femoral head on the image data, defining a sphere from these four points, and defining the center of the sphere as the hip center.

43. The method for planning a surgery of claim 42, wherein the four points, the computer image of the sphere, and the image data of the femoral head are displayed on the visual display means.

44. The method for planning a surgery of claim 42, wherein the four points are automatically identified by software programmed to find the four points.

45. The method for planning a surgery of claim 29, wherein the step of identifying a knee center comprises the steps of identifying epicondyle points on each of a femoral lateral epicondyle and a femoral medial epicondyle, defining a line segment connecting the epicondyle points, and defining the midpoint of that line segment as the knee center.

46. The method for planning a surgery of claim 29, wherein the step of identifying an ankle center comprises the steps of identifying malleoli points on each of a medial malleoli and a lateral malleoli on the three-dimensional computer model, defining a line segment connecting the malleoli points, and defining the midpoint of that line segment as the ankle center.

47. The method of planning surgery of claim 29, wherein the hip center, knee center, ankle center are displayed on the visual display means.

48. The method for planning surgery of claim 47, wherein the lines from the hip center to the knee center, and from the knee center to the ankle center, are displayed on the visual display means.

49. The method for planning surgery of claim 45, further comprising the steps (a) identifying on the three-dimensional computer model the femoral condyle on which the arthroplasty is to be performed; (b) translating the knee center to the origin of a Cartesian coordinate system; (c) rotating the three-dimensional computer model until the hip center lies on a coordinate axis; (d) rotating the three-dimensional computer model about the selected coordinate axis until the plane formed by the hip center and the epicondyle points is parallel to a coordinate plane formed using the selected coordinate axis, so that the line from the hip center to the knee center is aligned with the selected coordinate axis; (e) selecting a vertex on the three-dimensional computer model of the opposite femoral condyle that has the lowest value along the selected coordinate axis; (f) defining a rotation axis as the line perpendicular to the selected coordinate plane through the selected point; and, (g) rotating the three-dimensional computer model of the tibia about the rotation axis until the alignment has been accomplished.

50. The method of planning surgery of claim 49, wherein the selected point, the rotation axis, and the varus/valgus correction are identified by software stored in the computer.

51. The method for planning surgery of claim 29, wherein size and three-dimensional image data for each of the femoral and tibial prosthetic components is stored in a second memory means accessible by the computer, and further comprising the step of determining the size and pose of the prosthesis components by comparing the three-dimensional computer model of the femur and tibia with the prothesis size and image data.

52. The method for planning surgery of claim 51, wherein the three-dimensional prothesis image data is displayed on the visual display means superimposed on the three-dimensional computer model of the femur and tibia, and wherein the size and pose of the three-dimensional prosthesis image are adjusted to fit the three-dimensional computer model to a degree sufficient to accomplish the defined desired varus/valgus correction.

53. The method for planning surgery of claim 52, wherein at least two three-dimensional images of different sizes of the femoral prosthetic component and the tibial prosthetic component are displayed on the visual display means superimposed on the three-dimensional computer model of the femur and the tibia, and wherein a three-dimensional image of the femoral prosthetic component of a particular size, and a three-dimensional image of the tibial prosthetic component of a particular size, are chosen to fit the three-dimensional computer model to a degree sufficient to accomplish the defined desired varus/valgus correction.

54. The method for planning surgery of claim 53, wherein at least two three-dimensional images of different sizes of the femoral prosthetic component and the tibial prosthetic component are displayed on the visual display means superimposed on the three-dimensional computer model of the femur and the tibia, and wherein an operator chooses a three-dimensional image of the femoral prosthetic component of a particular size, and a three-dimensional image of the tibial prosthetic component of a particular size, to fit the three-dimensional computer model to a degree sufficient to accomplish the defined desired varus/valgus correction.

55. The method for planning surgery of claim 29, wherein the resections of each of the femur and tibia are shown in relation to the three-dimensional computer model of the femur and tibia and displayed on the visual display means.

* * * * *